(12) United States Patent
Ma et al.

(10) Patent No.: US 7,755,068 B2
(45) Date of Patent: Jul. 13, 2010

(54) LASER-ACCELERATED PROTON THERAPY UNITS AND SUPERCONDUCTING ELECTROMAGNET SYSTEMS FOR SAME

(75) Inventors: Chang Ming Ma, Huntingdon Valley, PA (US); Eugene S Fourkal, Philadelphia, PA (US); Jinsheng Li, Maple Glen, PA (US); Wei Luo, Chapel Hill, NC (US)

(73) Assignee: Fox Chase Cancer Center, Philadelphia, PA (US)

( * ) Notice: Subject to any disclaimer, the term of this patent is extended or adjusted under 35 U.S.C. 154(b) by 160 days.

(21) Appl. No.: 11/720,873

(22) PCT Filed: Dec. 21, 2005

(86) PCT No.: PCT/US2005/046834

§ 371 (c)(1),
(2), (4) Date: Sep. 5, 2008

(87) PCT Pub. No.: WO2007/061426

PCT Pub. Date: May 31, 2007

(65) Prior Publication Data

US 2009/0050819 A1    Feb. 26, 2009

Related U.S. Application Data

(60) Provisional application No. 60/638,870, filed on Dec. 22, 2004.

(51) Int. Cl.
*G21K 5/04* (2006.01)
(52) U.S. Cl. .............. 250/492.3; 250/396 R; 250/396 ML; 250/491.1; 250/423 R; 600/1; 600/2

(58) Field of Classification Search .......... 250/396 R, 250/398, 400, 396 ML, 491.1, 492.1, 492.3, 250/423 R, 424, 423 P; 600/1, 2; 315/111.81
See application file for complete search history.

(56) References Cited

U.S. PATENT DOCUMENTS 3,789,832 A * 2/1974 Damadian ............... 600/410

(Continued)

FOREIGN PATENT DOCUMENTS

EP    0357368 B1    11/1993

(Continued)

OTHER PUBLICATIONS

Jakel, et al. "Selection of beam angles for radiotherapy of skull base tumours using charged particles", *Physics in Medicine & Biology*, vol. 45, 2000, 1229-1241.

(Continued)

*Primary Examiner*—Jack I Berman
*Assistant Examiner*—Nicole Ippolito Rausch
(74) *Attorney, Agent, or Firm*—Woodcock Washburn, LLP

(57) ABSTRACT

Compact particle selection and collimation devices are disclosed for delivering beams of ions with desired energy spectra. These devices are useful with laser-accelerated ion therapy systems, in which the initial ions have broad energy and angular distributions. Superconducting electromagnet systems produce a desired magnetic field configuration to spread the ions with different energies and emitting angles for particle selection. The simulation of ion transport in the presence of the magnetic field shows that the selected ions are successfully refocused on the beam axis after passing through the magnetic field. Dose distributions are also provided using Monte Carlo simulations of the laser-accelerated ion beams for radiation therapy applications.

34 Claims, 15 Drawing Sheets

U.S. PATENT DOCUMENTS

| | | | |
|---|---|---|---|
| 4,199,402 A | 4/1980 | Ahmed | |
| 6,034,377 A | 3/2000 | Pu | |
| 6,683,318 B1 * | 1/2004 | Haberer et al. | 250/492.3 |
| 6,852,985 B2 | 2/2005 | Cowan et al. | |
| 7,268,358 B2 | 9/2007 | Ma et al. | |
| 7,317,192 B2 | 1/2008 | Ma et al. | |
| 2003/0165213 A1 * | 9/2003 | Maglich | 376/159 |
| 2006/0016728 A1 * | 1/2006 | Shorts | 209/1 |
| 2006/0145088 A1 | 7/2006 | Ma et al. | |
| 2007/0034812 A1 | 2/2007 | Ma et al. | |

FOREIGN PATENT DOCUMENTS

| | | |
|---|---|---|
| WO | WO99/03314 A1 | 1/1999 |
| WO | WO2004/109717 A3 | 12/2004 |
| WO | WO2005/057738 A2 | 6/2005 |

OTHER PUBLICATIONS

Prelec, "Ions and ion accelerators for cancer treatment", Fizika B, vol. 6, N4, 1997, retried from internet on Sep. 9, 2008 url : http://fizika.hfd.hr/fizia_b/bv97/b6p177.pdf.

* cited by examiner

Figure 12
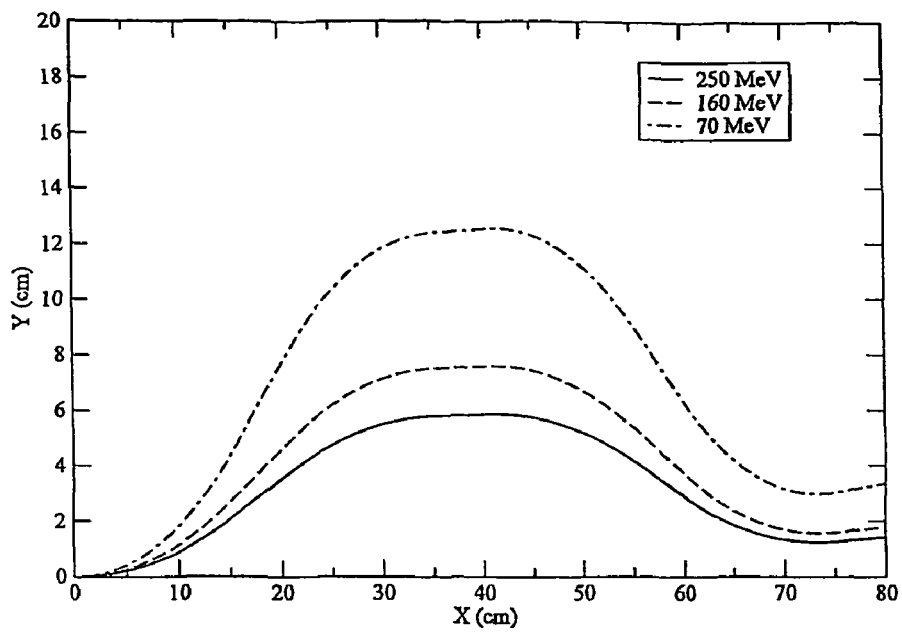
(a)
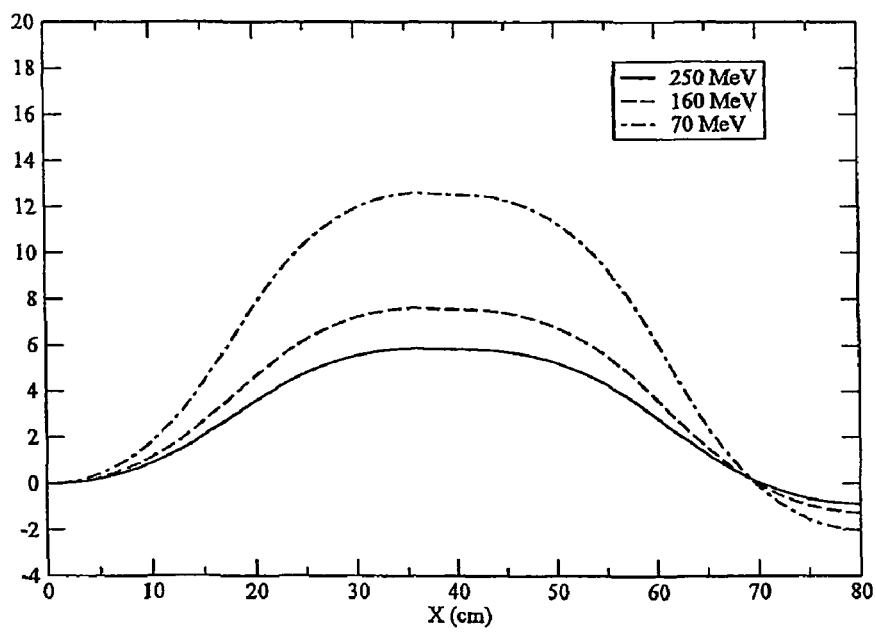
(b)

LASER-ACCELERATED PROTON THERAPY UNITS AND SUPERCONDUCTING ELECTROMAGNET SYSTEMS FOR SAME

CROSS-REFERENCE TO RELATED APPLICATIONS

This application is the National Stage of International Application No. PCT/US2005/046834, filed Dec. 21 2005, which claims the benefit of U.S. Provisional Application No. 60/638,870, filed Dec. 22, 2004, the disclosure of which is incorporated herein by reference in its entirety.

STATEMENT OF GOVERNMENT SUPPORT

This work is partly supported by the Department of Health and Human Services, the National Institute of Health, and the Department of Defense, under contract numbers NIH CA78331 and DOD PC030800, respectively. Accordingly, the Government may have rights in these inventions.

FIELD OF THE INVENTION

The present invention pertains to superconducting electromagnet systems for manipulating charged particles. The present invention also pertains to providing high energy positive ions for radiation therapy.

BACKGROUND OF THE INVENTION

In radiation therapy, the use of proton beams provides the possibility of better dose conformity to the treatment target and normal tissue sparing compared to commonly used photon beams because of the lower entrance dose, sharper penumbra and rapid fall off beyond the treatment depth, which result from the Bragg peak in the dose distribution. Despite the dosimetric superiority and some encouraging clinical results for well-localized radio-resistant lesions, the utilization of proton therapy has lagged behind therapies using photons and electrons because the facilities of proton therapy employing cyclotron and synchrotron technology are expensive and complex. As a result, proton therapy has not been a widespread modality in radiation therapy. This situation can be improved if a compact and economical laser-proton therapy unit is available. Laser-proton systems for radiation therapy are currently being developed at the Fox Chase Cancer Center, Philadelphia, Pa. by the present inventors. A typical laser-proton system design includes three types of components: (1) a compact laser-proton source to produce high-energy protons, (2) a compact particle selection and beam collimating device for accurate beam delivery, and (3) a treatment optimization algorithm to achieve conformal dose distributions using laser-accelerated proton beams.

Laser acceleration of particles was first proposed in 1979 for electrons. Rapid progress has been made in laser-electron acceleration in the 1990s since the advent of chirped pulse amplification (CPA) and high fluence solid-state laser materials such as Ti:sapphire. Recently, there have been a number of experimental investigations, which observed protons with energies of several tens of MeV. A recent experiment conducted at Lawrence Livermore National Laboratory reported particles with a maximum energy of 58 MeV. The mechanism for laser-proton acceleration is under study. It has been long linked to the longitudinal electric field created as a result of laser-matter interaction. Recent experimental investigations as well as the results of computer simulations (specifically particle in cell) of the laser-plasma interaction for proton acceleration have shown that laser-accelerated proton beams have broad energy and angular distributions and cannot be directly used in therapy.

A spectrometer-like particle selection and beam modulation system is described by several of the present inventors in which a magnetic field distributed as a step function was used to spread protons in space according to their energies and emitting angles. A particle selection and beam modulation system has been disclosed in International Patent Application No. PCT/US2004/017081, filed Jun. 2, 2004, entitled "High Energy Polyenergetic Ion Selection Systems, Ion Beam Therapy Systems, and Ion Beam Treatment Centers", the entirety of which is incorporated by reference herein. Subsequently, the proton beams are retrieved with resultant energies, which can be used to generate modulated energy distributions that will deliver the spread-out Bragg Peaks (SOBP). Therefore, the earlier proposed particle selection system constitutes a selection device, which is based on the ideal step field configuration. As a step field distribution is difficult to achieve, further improvements to-particle selection systems that incorporate non-ideal step field configurations are presently needed. Also because non-step field configurations arise from the use of typical electromagnet systems, improvements in the electromagnet systems are currently sought for the efficient and compact separation of laser-accelerated polyenergetic positive ions.

SUMMARY OF THE INVENTION

The present invention provides compact superconducting electromagnet systems capable of producing a step-like magnetic field distribution, which can be useful for proton beam selection. One design of the superconducting electromagnet system can be obtained from an analytical calculation of the magnetic field for rectangular coils, which provides a three dimensional magnetic field distribution, thus accounting for such boundary effects as edge focusing due to the influence of the flinging field patterns at the edge of the coils. The simulation of proton trajectories can be used to test the electromagnet system and optimize the design for certain criteria.

In certain embodiments, the electromagnets of the invention are capable of producing a step-like magnetic field for use in a high energy polyenergetic positive ion beam selection mechanism.

The present invention also provides superconducting electromagnet systems that produce step-like fields distributed in rectangular regions. The field distributions are useful for proton transport in particle selection systems. Proton dose distributions are calculated and compared to the results for the ideal step field and the field that can be generated by the designed superconducting electromagnet system.

The present invention provides for ion selection systems for high energy polyenergetic ion beams composed of a plurality of high energy polyenergetic positive ions. These systems are composed of a beam collimator, a first magnetic field source capable of spatially separating said high energy polyenergetic positive ions according to their energy levels, an aperture capable of modulating the spatially separated high energy polyenergetic positive ions, and a second magnetic field source capable of recombining the modulated high energy polyenergetic positive ions, where the first and second magnetic field sources are superconducting electromagnets capable of providing a magnetic field of about 0.1 to about 30 Tesla.

There are also provided methods of forming a high energy polyenergetic positive ion beam comprising the steps of forming a laser-accelerated high energy polyenergetic ion beam composed of a plurality of high energy polyenergetic positive ions characterized as having a distribution of energy levels, collimating the laser-accelerated ion beam using a collimation device, spatially separating the high energy positive ions according to their energy levels using a first magnetic field provided by a first superconducting electromagnet having a magnetic field of about 0.1 to 30 Tesla, modulating the spatially separated high energy polyenergetic positive ions using an aperture; and then recombining the modulated high energy polyenergetic positive ions using a second magnetic field provided by a second superconducting electromagnet having a magnetic field of at least about 0.1 to about 30 Tesla.

Also provided are laser-accelerated high energy polyenergetic positive ion therapy systems. These systems comprise a laser-targeting system, comprising a laser and a targeting system capable of producing a high energy polyenergetic ion beam, an ion selection system capable of producing a therapeutically suitable high energy polyenergetic positive ion beam from a portion of said high energy polyenergetic positive ions, said ion selection system comprising at least two superconducting electromagnets each capable of providing a magnetic field of about 0.1 to about 30 Tesla, and an ion beam monitoring and control system. The high energy polyenergetic ion beam in these systems can be comprised of high energy polyenergetic positive ions having energy levels of at least about 50 MeV, with the high energy polyenergetic positive ions being spatially separated based on energy level.

The present invention also provides methods of treating a patient with a laser-accelerated high energy polyenergetic positive ion therapy system. These methods of treatment comprise the steps of identifying the position of a targeted region in a patient, determining the treatment strategy of the targeted region, with the treatment strategy comprised of determining the dose distributions of a plurality of therapeutically suitable high energy polyenergetic positive ion beams for irradiating the targeted region, forming said plurality of therapeutically suitable high energy polyenergetic positive ion beams from a plurality of high energy polyenergetic positive ions, that are spatially separated based on energy level using one or more superconducting electromagnets each capable of providing a magnetic field of about 0.1 to about 30 Tesla, and delivering the plurality of therapeutically suitable polyenergetic positive ion beams to the targeted region according to the treatment strategy.

Also provided are laser-accelerated high energy polyenergetic positive ion beam treatment centers. These centers comprise a location for securing a patient and a laser-accelerated high energy polyenergetic positive ion therapy system capable of delivering a therapeutically suitable high energy polyenergetic positive ion beam to a patient at said location This ion therapy system can be comprised of a laser-targeting system, said laser-targeting system comprising a laser and a target assembly capable of producing a high energy polyenergetic ion beam, comprising high energy polyenergetic positive ions having energy levels of at least about 50 MeV, an ion selection system capable of producing a therapeutically suitable high energy polyenergetic positive ion beam using said high energy polyenergetic positive ions, the high energy polyenergetic positive ions being spatially separated based on energy level using superconducting electromagnets each capable of providing a magnetic field of about 0.1 to about 30 Tesla, and a monitoring and control system for the therapeutically suitable high energy polyenergetic positive ion beam.

Further, there are provided compact superconducting electromagnet systems for magnetically separating a polyenergetic positive ion beam. These systems comprise a series of two or more superconducting coils in fluidic communication. Each of the superconducting coils can be individually capable of providing a magnetic field of about 0.1 to about 30 Tesla and at least two of the magnetic fields are provided in opposite directions to each other.

These and other aspects of the present invention will be readily be apparent to those skilled in the art in view of the following drawings and detailed description. The summary and the following detailed description are not to be considered restrictive of the invention as defined in the appended claims and serve only to provide examples and explanations of the invention.

BRIEF DESCRIPTION OF THE DRAWINGS

The foregoing summary, as well as the following detailed description, is further understood when read in conjunction with the appended drawings. For the purpose of illustrating the invention, there is shown in the drawings exemplary embodiments of the invention; however, the invention is not limited to the specific methods, compositions, and devices disclosed. In the drawings:

FIG. 12 depicts proton trajectories for different widths of the middle electromagnets: (a) $L_x$=15 cm. (b) $L_x$=17 cm.

DETAILED DESCRIPTION AND ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

As used herein, the term "protons" refers to the atomic nuclei of hydrogen ($H^1$) having a charge of +1.

As used herein, the term "positive ions" refers to atoms and atomic nuclei having a net positive charge.

As used herein, the term "polyenergetic" refers to a state of matter being characterized as having more than one energy level.

As used herein, the term "high energy" refers to a state of matter being characterized as having an energy level greater than 1 million electron volts ("MeV").

As used herein, the term "beamlet" refers to a portion of a high energy polyenergetic positive ion beam that is spatially separated, or energetically separated, or both spatially and energetically separated.

The terms "primary collimator", "primary collimation device", "initial collimator", and "initial collimation device" are used interchangeably herein.

The terms "energy modulation system" and "aperture" are used interchangeably when it is apparent that the aperture referred to is capable of modulating a spatially separated high energy polyenergetic positive ion beam.

Figure 2:
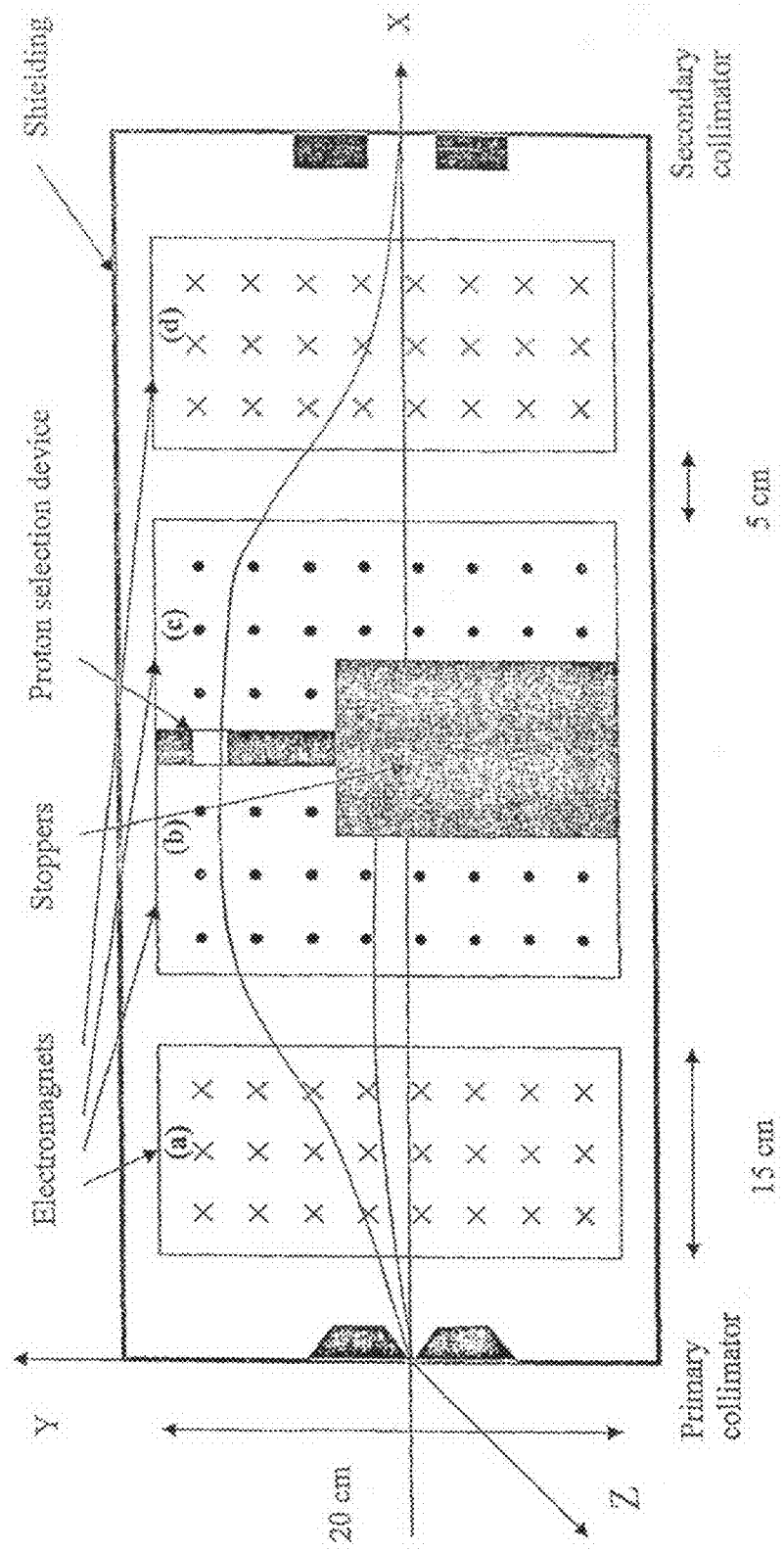
FIG. 2 is a schematic description of an embodiment of a proton selection system of the invention. Protons are produced right before the primary collimator and travel in the magnetic field generated by the superconducting electromagnet system. The desired protons move initially towards the X-axis, deflect in the field, and return to the X-axis after traversing the magnetic field. Those unwanted particles are either stopped by the stoppers and collimators, or absorbed by the surrounding shielding.

The phrase "fluidic communication" is meant that two or more electromagnetic coils are arranged such that one or more ion beams is capable of passing through the magnetic field generated within each of the coils, such as illustrated in FIG. 2.

The ion selection systems for high energy polyenergetic ion beams are composed of a beam collimator, a first magnetic field source capable of spatially separating said high energy polyenergetic positive ions according to their energy levels, an aperture capable of modulating the spatially separated high energy polyenergetic positive ions, and a second magnetic field source capable of recombining the modulated high energy polyenergetic positive ions, where the first and second magnetic field sources are superconducting electromagnets capable of providing a magnetic field of about 0.1 to about 30 Tesla. Laser-accelerated proton therapy systems use high intensity laser pulses to generate plasmas in a high density material, and accelerate the protons to high kinetic energies. Examples of laser-accelerated proton therapy systems that can be adapted for use in the present invention are described in further detail in "High Energy Polyenergetic Ion Selection Systems, Ion Beam Therapy Systems, and Ion Beam Treatment Centers", WO2004109717, U.S. application Ser. No. 10/559058, claiming priority to U.S. App. No. 60/475,027, filed Jun. 2, 2003, the portion of which pertaining to laser-accelerated proton therapy systems is incorporated by reference herein. Examples of methods of modulating laser-accelerated protons for radiation therapy that can be adapted for use in the present invention are described in further detail in "Methods of Modulating Laser-Accelerated Protons for Radiation Therapy", WO2005057738, U.S. application Ser. No. 11/445850, claiming priority to U.S. App. No. 60/475,027, filed Jun. 2, 2003, and U.S. App. No. 60/526,436, filed Dec. 2, 2003, the portion of which pertaining to methods of modulating laser-accelerated protons for radiation therapy is incorporated by reference herein.

The compact superconducting electromagnet systems for magnetically separating a polyenergetic positive ion beam in some embodiments include a series of two or more superconducting coils in fluidic communication. Each of the superconducting coils is individually capable of providing a magnetic field of between about 0.1 and about 30 Tesla, and at least two of the magnetic fields are provided in opposite directions to each other.

In some embodiments, the compact superconducting electromagnet systems include two outer electromagnets each capable of providing a magnetic field in the same direction, and two inner electromagnets each capable of providing a magnetic field in the same direction to each other and opposite the direction of the magnetic field of the outer electromagnets. In these embodiments, the magnetic fields of the inner electromagnets may by different in strength, or they may have about the same strength. In related embodiments, the two inner electromagnets can be adjacent to each other or separated by a gap. When separated, a suitable gap is typically in the range of from about 0.2 cm to about 5 cm, and more suitably in the range of from about 0.5 to about 2 cm. In certain preferred embodiments, the two inner electromagnets are separated by a gap of about 1 cm. In certain embodiments, a series of collimators each having an aperture size in the range of from about 0.02 cm to about 2 cm.

Strong magnetic fields can be generated using the superconducting electromagnet systems. Compact superconducting electromagnet systems can include electromagnets that are variously shaped to control the magnetic field distribution. In certain embodiments the superconducting electromagnetic coils are preferably shaped to produce uniformly distributed fields. Suitable superconducting electromagnets are rectangularly shaped. Rectangularly shaped superconducting electromagnets are capable of producing magnetic fields that are more uniformly spatially distributed than magnetic fields arising from circularly shaped electromagnets.

Suitable magnetic field sources for this and various embodiments of the present invention include superconducting electromagnets having a magnetic field strength in the range of from about 0.1 to about 30 Tesla, more suitably in the range of from about 0.2 to 20 Tesla, or even from about 0.5 to about 10 Tesla, and more suitably in the range of from about 0.5 to about 5 Tesla. In some embodiments, the maximum magnetic field of each of the electromagnets can be less than about 5 Tesla. In certain embodiments, superconducting electromagnets having from about 1,000 to about 100,000 turns, preferably from about 5,000 to about 20,000 turns, and even more preferably about 10,000 turns are suitable for the present invention.

Suitable superconducting electromagnet can be made by winding a long wire by multiple turns. Two or more such superconducting electromagnets can be connected together, which provide a gap, d, between, where a somewhat uniform magnetic field can be provided and protons will pass therethrough. The dimensions of a single superconducting electromagnet can be determined with both the laser-proton system design and the selection of the material of the wire in mind. A compact laser-proton system can include a compact electromagnet system. In some embodiments, the dimensions of the superconducting electromagnets can be rectangular in over all shape, having rectangular dimensions in the range of from about 5 cm to about 100 cm, more preferably in the range of from about 10 cm to about 75 cm, and even more preferably in the range of from about 15 cm to 50 cm. In one embodiment of the present invention, the upper limit on the dimensions of a single superconducting electromagnet can be set to about $20 \times 40 \times 25$ cm$^3$ ($L_x \times L_y \times L_z$). As used herein, the mathematical symbol tilde ("~") used in front of a number means "about". If a conventional copper wire is used, which can carry a current with a density of ~$10^3$ A/cm$^2$, the cross sector of the electromagnet coil wound with the copper wire should be ~$10^3$ cm$^2$ to get a total current of ~$10^6$ A to achieve a magnetic induction of ~4.4 T (see Appendix). Thus, a thickness (T) of about 40 cm for a conventional non-superconducting electromagnet with a length ($L_z$) of about 25 cm can be used to meet the cross section, which makes the width in both x- ($L_x$) and y-direction, ($L_y$) much greater than about 80 cm. While such electromagnets can be used in the present invention, it may be desirable to use even smaller electromagnets.

The size of the electromagnet can be significantly reduced by utilizing superconducting wires instead of copper because a superconducting wire can carry a very high current density. Another advantage of using superconducting wires can be saving power. The power consumption for a superconducting electromagnet is only about 1% to about 10% of that for a comparable conventional electromagnet. Superconducting wires are commercially available and have been widely used in high energy accelerators to produce strong magnetic fields. A suitable superconducting wire can be NbTi, which has a critical current density of ~$4.25 \times 10^5$ A/cm$^2$ at 4.2 K for a field of ~4.4 T. Another commercially available superconducting wire, Nb$_3$Sn, can also be used. Other types of superconducting wires, including those made from high temperature superconductors, can be used. Suitable high temperature superconducting wires have a critical temperature above about 77 K, examples of which include YBCO (e.g., YBa$_2$Cu$_3$O$_{7-x}$) and BSCCO (e.g., Bi$_2$Sr$_2$Ca$_2$Cu$_3$O$_{10}$ or Bi$_2$Sr$_2$Ca$_1$Cu$_2$O$_8$) materials. Suitable high temperature superconducting wires are commercially available from the American Superconductor, Westborough, Mass., (http://www.amsuper.com/index.cfm). Suitable superconducting wires, such as NbTi wires, are commercially available in widths of from about 10 micron to 250 micron diameter form Japan Superconducting Technology, Inc. Tokyo, Japan, (http://www.jastec.org/eg/index.html). The actual current can be less than the critical current, otherwise, the superconducting state can be broken and the wire will function in the conventional conducting state.

In one embodiment, four electromagnets can be used to achieve a step-like field distribution. The electromagnets are placed parallel along the x-axis (beam axis) with the first and the fourth electromagnet field pointing to −z, and the second and third magnetic field pointing to z. The first electromagnet produces the magnetic field with the Lorentz force that pushes protons up, then the second and the third produce the field that pulls the protons down, and the field from the last one puts the protons back to the original direction. Such a superconducting electromagnet system can be shorter than about 100 cm in the dimension along the beam axis.

Suitable cryogenics for the superconducting electromagnets used in the present invention may include any of the cryogenic systems know to those skilled in the art, which are readily fashioned from commercially available components for superconducting electromagnets. A suitable cryostat can be designed and implemented together with the electromagnet system.

In various embodiments, an initial collimator defines the angular spread of the incoming beam entering the first magnetic field. The tangent of the angle of the beam spread of the beam exiting the initial collimator can be about the ratio of one half the distance of the initial collimator exit opening where the beam exits the collimator to the distance of the collimator exit opening to the proton beam source (i.e., the plasma target). This angle can be less than about 1 radian. The emitting angle is the angle of the initial energy distribution exiting the target system (i.e., target and initial collimation device). Electrons can be deflected in the opposite direction from the positive ions by the first magnetic field and absorbed by a suitable electron beam stopper. Suitable electron stoppers include tungsten, lead, copper or any material of sufficient thickness to attenuate the electrons and any particles they generate to a desired level. The aperture can be used to select the desired energy components, and the matching magnetic field setup (in one embodiment, the second magnetic field) can be selected that is capable of recombining the selected protons into a polyenergetic positive ion beam. Suitable apertures can be made from tungsten, copper or any other materials of sufficient thickness that are capable of reducing the energy levels of positive ions. This energy level reduction can be carried out to such a degree that the positive ions can be differentiated from those ions that do not go through the aperture.

In various embodiments of the present invention, the aperture geometry can be a circular, rectangular, or irregular-shaped opening or multiple openings on a plate or slab, which when placed in a spatially separated polyenergetic ion beam, is capable of fluidically communicating a portion of the ion beam therethrough. In other embodiments, the aperture can be made from a plate that has multiple openings that are controllably selected, such as by physical translation or rotation into the separated ion beam to spatially select the desirable energy level or energy levels to modulate-the separated ion beam. The modulation of the ion beam gives rise to a therapeutically suitable high energy polyenergetic positive ion beam as described herein. Suitable apertures include multi-leaf collimators. In addition to controllably selecting the spatial position of the openings that fluidically communicate the spatially separated ion beams, the aperture openings may also be controllably shaped or multiply shaped, using regular or irregular shapes. Various combinations of openings in the aperture are thus used to modulate the spatially separated ion beam. The spatially separated positive ions are subsequently recombined using the second magnetic field.

The high and low energy positive ion (e.g., proton beam) stoppers can eliminate unwanted low-energy particles and high-energy particles (not shown). Because of the broad angular distribution of the accelerated protons (which depends on a given energy range), there can be a spatial mixing of different energy positive ions after they pass through the first magnetic field. For example, a portion of the low energy protons may go to regions where the high energy particles reside, and vice versa. Reducing the spatial mixing of protons can be carried out by introducing a primary collimation device, such as the initial collimation device. A primary collimation device can be used to collimate protons to the desired angular distribution.

To reduce the unwanted protons, as well as to collimate them to a specific angular distribution, a primary collimation device can be provided. Its geometrical size and shape can be tailored to the energy and angular proton distributions. For example, in one embodiment of the present invention there can be provided a 5 cm long tungsten collimator that absorbs the unwanted energy components. Because of its density and the requirement for the compactness of the selection system, tungsten is a favorable choice for collimation purposes. A suitable primary collimator opening provides a 1×1 cm² field size defined at 100 cm SSD. Protons that move into an angle larger than this can be blocked. The magnetic field spreads the polyenergetic protons into spatial regions according to their energy and angular distributions. Their spatial distribution can be such that the lower energy particles are deflected at greater distances away from the central axis, and as the proton energy increases the spatial deflection decreases. Therefore, the contribution of both the magnetic field and the primary collimator (with a specific collimator opening) creates such a spatial proton distribution that allows the energy selection or proton energy spectrum reformation, using an aperture. The geometric shape of an aperture can determine the energy distribution of the therapeutic protons.

One embodiment of the present invention provides an ion-selection system in which a magnetic field is used to spread the laser-accelerated protons spatially based on their energy levels and emitting angles, and apertures of different shapes are used to select protons within a therapeutic window of energy and angle. Such a compact device eliminates the need for the massive beam transportation and collimating equipment that is common in conventional proton therapy systems. The laser-proton source and the ion selection and collimating device of the present invention can be installed on a treatment gantry (such as provided by a conventional clinical accelerator) to form a compact treatment unit, which can be installed in a conventional radiotherapy treatment room.

In certain embodiments of the invention, a secondary monitor chamber measures the intensity of each energy component. A primary monitor chamber can be also provided. Various ways of monitoring ion beams and control systems are disclosed in U.S. patent application Ser. No. 09/757,150 filed Jan. 8, 2001, Pub. No. U.S. 2002/0090194 A1, Pub. Date Jul. 11, 2002, "Laser Driven Ion Accelerator", the portion of which pertaining to monitoring ion beams and control systems is incorporated by reference herein.

One embodiment of a suitable compact geometry provides dimensions of less than 50 cm in length and less than 40 cm in diameter. Since different laser-protons have different angular distributions, a collimator can be used to define the field size. When the initial collimator has a square opening, and the polyenergetic collimated protons of different energy levels have passed through the electromagnet fields, the collimated protons will reach different transverse locations. Because of the finite size of the initial collimator there can be some overlap of proton energy levels, which can depend on the size of the initial collimator, the magnetic field strength and the distance from the energy plane to the initial collimator. For selecting the desired energy of this embodiment, a second collimator can be used, which can be positioned at the corresponding transverse location. For example, a square aperture can be used to select a 50, 150 or the 250 MeV field of protons. Multiple laser pulses can be provided to produce a combination of protons to provide a desired spectrum. The desired proton energy spectrum can be used to produce a therapeutically high energy polyenergetic positive ion beam, which provides uniform dose distributions over a desired depth range.

Another embodiment of the ion selection system of the present invention is to use variable aperture sizes at the energy space (plane) to select both an energy and the total number of protons of that energy (intensity) simultaneously. This embodiment uses fewer laser pulses to achieve a desired proton spectrum compared to the preceding embodiment. This variable aperture size embodiment preferably uses an elongated aperture at the energy space with variable widths at different transverse (energy) locations. Without being bound by a particular theory of operation, this design allows for energy and intensity selection simultaneously from the same laser pulse. This appears to be a highly efficient way to use a polyenergetic laser-proton beam to achieve a uniform dose over a depth range for radiation therapy. A variable energy aperture size can use a subsequent differential magnetic system to recombine the fields of different proton energy levels to a similar field size.

In certain embodiments, a secondary collimation device can be provided to define the final field size and shape of the positive ions that form the therapeutically suitable high energy polyenergetic positive ion beam. Small shaped beams (e.g., squares, circles, rectangles, and combinations thereof) can be provided by modulating the intensity of individual beamlets so that a conformal dose distribution to the target volume can be achieved.

In this embodiment, there is provided a modulatable secondary collimation device that is capable of modulating the spatially separated beam. The modulatable secondary collimation device may have a variable shape, which can be realized using an aperture, as described earlier, such as a multileaf collimator (MLC). A number of laser pulses can be provided using this embodiment to treat a target volume. While the aperture that modulates the energy levels can move in the transverse direction to select a desired energy spectrum to cover the depth range of at least a portion of the entire target volume, the modulatable secondary collimation devices (e.g., the MLC) are capable of changing the field shape of the recombined beam to enclose at least a portion of the cross-section of the target volume at the corresponding depths.

The methods described herein for the ion selection systems of the present invention may suitably be performed using the devices and instrumentalities described herein. Because the proton beams can be small in cross-section, it is possible to establish a high magnetic field within a small space. Certain embodiments of the present invention do not require strict B-field spatial distribution, rather, the magnetic fields may have a slow gradient, they may be spatially overlapping, or both. Suitable embodiments of the present invention will include at least two magnetic field sources that have matching, opposite, B-fields. The geometry may be further reduced in the beam direction by using higher magnetic fields, smaller photon beam stoppers, or both.

Various alternate embodiments of the present invention include embodiments of an ion selection system composed of a collimation device capable of collimating a laser-accelerated high energy polyenergetic positive ion beam, the laser-accelerated high energy polyenergetic ion beam having a plurality of high energy polyenergetic positive ions; a first magnetic field source capable of spatially separating the high energy polyenergetic positive ions according to their energy levels; an aperture capable of modulating the spatially separated high energy polyenergetic positive ions; and a second magnetic field source capable of recombining the modulated high energy polyenergetic positive ions, wherein the first and second magnetic field sources are provided are superconducting electromagnets capable of providing a magnetic field between about 0.1 and about 30 Tesla.

Another embodiment of an ion selection system similar to that provided above further includes a third magnetic field source, the third magnetic field source capable of bending the trajectories of the spatially separated high energy polyenergetic positive ions towards the aperture. Preferably the third magnetic field source is a superconducting electromagnet. Additional embodiments include an ion selection system similar to the above but with the aperture placed inside the magnetic field of the third magnetic field source or alternatively, with the aperture being placed outside of the magnetic field of the third magnetic field source, where the third magnetic field source is separated into two portions.

In other embodiments of the invention, the magnetic field of the third magnetic field source is capable of bending the trajectories of the modulated high energy polyenergetic positive ions towards the second magnetic field source. In certain embodiments, the second magnetic field source is capable of bending the trajectories of the modulated high energy polyenergetic positive ions towards a direction that is not parallel to the direction of the laser-accelerated high energy polyenergetic ion beam. Other embodiments have a second magnetic field source that is capable of bending the trajectories of the modulated high energy polyenergetic positive ions towards a direction that is parallel to the direction of the laser-accelerated high energy polyenergetic ion beam.

Certain embodiments of the invention have a secondary collimation device capable of fluidically communicating a portion of the recombined high energy polyenergetic positive ions therethrough. In certain embodiments, the secondary collimation device is capable of modulating the beam shape of the recombined high energy polyenergetic positive ions. In certain embodiments, a rotatable wheel with an aperture having a plurality of openings, each of the openings capable of fluidically communicating high energy polyenergetic positive ions therethrough, can be used. Another suitable aperture is a multileaf collimator with openings that are capable of passing low energy ions, high energy ions, respectively, or a combination thereof.

In accordance with certain embodiments of the invention, a laser-accelerated high energy polyenergetic ion beam including a plurality of high energy polyenergetic positive ions is collimated using a collimation device, and the positive ions are spatially separated according to their energy levels using a first magnetic field. The spatially separated high energy polyenergetic positive ions are modulated using an energy selection aperture and the modulated high energy polyenergetic positive ions are recombined using a second magnetic field. In certain embodiments, a portion of the positive ions are transmitted through the aperture, e.g., having energy levels in the range of from about 50 MeV to about 250 MeV, and other portions are blocked by the energy selection aperture. In this embodiment magnetic fields of strength between about 0.1 and about 30 Tesla are provided using superconducting electromagnets. In certain embodiments, the magnetic field is between about 0.2 and about 20 Tesla.

In certain embodiments, the trajectories of the positive ions are bent in a direction away from the beam axis of the laser-accelerated high energy polyenergetic ion beam using the first magnetic field. In other embodiments, the trajectories of the spatially separated positive ions are further bent in a direction towards the aperture using the third magnetic field. The third magnetic field, in some embodiments, bends the trajectories of the spatially separated high energy polyenergetic positive ions towards the second magnetic field. This embodiment can further include the bending of the trajectories of the ions by the second magnetic field toward a direction parallel to the direction of the laser-accelerated high energy polyenergetic ion beam. Preferably, the first second and third magnetic fields are supplied by superconducting electromagnets. In certain embodiments, the spatially separated high energy positive ions are modulated by energy level using a location-controllable opening in an aperture. In some embodiments, the spatial separation of the high energy polyenergetic positive ions is over distances up to about 50 cm with these distances measured perpendicularly to the beam axis of the laser-accelerated ion beam as it enters the first magnetic field.

The present invention also provides methods of producing radioisotopes using the laser-accelerated high energy polyenergetic ion beams provided herein by irradiating a radioisotope precursor with the recombined spatially separated high energy polyenergetic positive ions. The production of 2-deoxy-2-18F fluoro-D-glucose ("[18F]FDG") is carried out by proton bombardment of the chemical precursors leading to the radioisotopes. These processes use proton beams generated using traditional cyclotron and synchrotron sources. For example, J. Medema, et al. [http://www.kvi.nl/~agorcalc/ecpm31/abstracts/medema2.html] have reported on the production of [18F] Fluoride and [18F] FDG by first preparing [18F] fluoride via the 18O (p, n) [18F] nuclear reaction in 18O enriched water, and producing the [18F]FDG by recovering the [18F]fluoride via the resin method and the cryptate drying process. The present invention provides high energy polyenergetic ion beams suitable for use in this process of preparing radioisotopes. Thus, the process of producing radioisotopes includes the steps of forming a high energy polyenergetic proton beam as described herein to provide an appropriate particle, target and beam current. A target precursor is filled with H218O. The high energy polyenergetic proton beam irradiates the target precursor until a preselected integrated beam current or time is reached. The target pressure can be monitored by a pressure transducer. When the integrated beam current or the time is reached the [18F] fluoride is used for chemically synthesizing [18F] FDG. The final product is isotonic, colorless, sterile, and pyrogen free and is suitable for clinical use.

The ion selection systems in various embodiments as described can be used as components of laser-accelerated high energy polyenergetic positive ion therapy systems. In one embodiment of the present invention there is provided a compact, flexible and cost-effective proton therapy system.

This embodiment relies on three technological breakthroughs: (1) laser-acceleration of high-energy polyenergetic protons, (2) compact system design for ion selection and beam collimation using superconducting electromagnets, and (3) treatment optimization software to utilize laser-accelerated proton beams. An important component of a laser proton radiotherapy system is a compact ion selection and beam collimation device, which is coupled to a compact laser-proton source to deliver small pencil beams of protons of different energy levels and intensities. Typically, the laser and the treatment unit are placed on the same suspension bench to ensure laser beam alignment (negligible energy loss due to the small distance). This also aids in keeping the whole system compact. In this embodiment, the target assembly and the ion selection device are placed on a rotating gantry and the laser beam is transported to the final focusing mirror through a series of mirrors. The distances between the mirrors are adjusted to scan the proton beam along x- and y-axis, respectively, which generates a parallel scanned beam. An alternative method is to swing the target and ion selection device about the laser beam axis defined by the mirrors to achieve a scan pattern. This generates a divergent scan beam. The treatment couch in the treatment system can be adjusted to perform coplanar and noncoplanar, isocentric and SSD (source-to-surface distance) treatments.

One embodiment of an ion therapy system includes a laser-targeting system, the laser-targeting system comprising a laser and a targeting system capable of producing a high energy polyenergetic ion beam, the high energy polyenergetic ion beam including high energy polyenergetic positive ions having energy levels of at least about 50 MeV. In this embodiment, the high energy polyenergetic positive ions are spatially separated based on energy level and an ion selection system capable of producing a therapeutically suitable high energy polyenergetic positive ion beam from a portion of the high energy polyenergetic positive ions is provided. Also provided is a differential chamber and an integration chamber. Positive ions of different energies will typically pass through different parts of the differential chamber that measure the differences in energies of the ions and monitors the energy of the selected ions. Typically, the differential chamber does not control the energy selection aperture. The integration chamber is provided to generate a signal that is analyzed (e.g., by a computer or suitable data processor) to determine the position of the aperture and the aperture openings.

One embodiment of the treatment system provides an ion-selection system in which a magnetic field is used to spread the laser-accelerated protons spatially based on their energy levels and emitting angles, and apertures of different shapes are used to select protons within a therapeutic window of energy and angle. To reduce the size of the ion-selection system, the magnetic field is supplied by superconducting electromagnets. The magnetic fields are typically in the range of about 0.1 and about 30 Tesla. Further embodiments use fields between about 0.2 and about 20 Tesla, about 0.5 and about 10 Tesla, and about 0.8 and about 5 Telsa. Using superconducting electromagnets results in a compact device that eliminates the need for the massive beam transportation and collimating equipment that is common in conventional proton therapy systems. The laser-proton source and the ion selection and collimating device of this embodiment are typically installed on a treatment gantry (such as provided by a conventional clinical accelerator) to form a compact treatment unit, which can be installed in a conventional radiotherapy treatment room.

A laser-accelerated high energy polyenergetic positive ion therapy system in the various embodiments described above can be used in a method of treating a patient. For example, the proton selection systems provided by the various embodiments of the present invention open up a way for generating small beamlets of polyenergetic protons that can be used for inverse treatment planning. Due to the dosimetric characteristics of protons, the energy and intensity modulated proton therapy can significantly improve the conformity of the dose to the treatment volume. In addition, healthy tissues are spared using the methods of the present invention compared to conventional treatments. Overall results suggest that the laser accelerated protons together with the ion selection system for radiation treatments will help treat cancer.

Radiation therapy is one of the most effective treatment modalities for prostate cancer. In external beam radiation therapy, the use of proton beams provides the possibility of superior dose conformity to the treatment target and normal tissue sparing as a result of the Bragg peak effect. While neutrons and photons (X-rays) show high entrance dose and slow attenuation with depth, monoenergetic protons have a very sharp peak of energy deposition as a function of the beam penetration just before propagation through tissue stops. As a consequence, it is possible for almost all of the incident proton energy to be deposited within or very near the 3D tumor volume, avoiding radiation-induced injury to surrounding normal tissues. Protons have a higher linear energy transfer component near the end of their range, and are more effective biologically for radiotherapy of deep-seated tumors than conventional medical accelerator beams or cobalt-60 sources.

In spite of the dosimetric superiority characterized by the sharp Bragg peak, utilization of proton therapy has lagged far behind that of photons for prostate treatment. This is because the operating regime for proton accelerators is at least an order of magnitude higher in cost and complexity, which results in their being too expensive for widespread clinical use compared to electron/photon medical accelerators. Conventional proton accelerators are cyclotrons and synchrotrons, of which only two such medical facilities exist in the U.S., those of Massachusetts General Hospital (MGH) and Loma Linda University Medical Center (LLUMC). Both occupy a very large space (entire floor or building). Although they are growing in number, only several such clinical facilities exist in the world. Despite a somewhat limited number of clinical cases from these facilities, treatment records have shown encouraging results particularly for well-localized radio resistant lesions. The degree of clinical effectiveness for a wide variety of malignancies has not been quantified due to limited treatment experience with this beam modality. This situation will be greatly improved by the availability of a compact, flexible, and cost-effective proton therapy system, as provided by the present invention. The present invention enables the widespread use of this superior beam modality and therefore bring significant advances in the management of cancers, such as brain, lung, breast and prostate cancers.

The method of treating a patient with a laser-accelerated high energy polyenergetic positive ion therapy system includes the step of determining the treatment strategy of the targeted region in the patient. The treatment strategy includes determining the dose distributions of a plurality of therapeutically suitable high energy polyenergetic positive ion beams for irradiation of the targeted region. Dose calculation is performed in treatment optimization for laser accelerated proton beam therapy because the dose distributions of small proton beamlets are significantly affected by the beam size and heterogeneous patient anatomy. Patient dose calculations are estimated using the GEANT3 system. The code is designed as a general purpose Monte Carlo simulation. For accelerating dose calculation, a fast proton dose calculation algorithm has been developed based on conventional photon and electron Monte Carlo dose calculation algorithms. Various variance reduction techniques have been implemented in the code to speed up the Monte Carlo simulation. These include "deterministic sampling" and "particle track repeating," which are very efficient for charged particle simulations. The implementation of this fast Monte Carlo code is tested using the GEANT3 code. The source models are also implemented to reconstruct the phase-space parameters (energy, charge, direction and location) for the proton pencil beams emerging from the laser proton therapy device during a Monte Carlo dose calculation. Suitable software is available that can be adapted for use in treating patients with laser-accelerated polyenergetic positive ions. Such software first converts the patient CT data into a simulation phantom consisting of air, tissue, lung and bone. Based on the contours of the target volume and critical structures, the software computes the dose distributions for all the beamlets of different spectra, incident angles (e.g., gantry angles specified by the planner), and incident locations (e.g., within a treatment port/field). The final dose array for all the beamlets is provided to the treatment optimization algorithm, as described further below.

In certain embodiments, improved treatment optimization tools for EIMPT are also provided. A treatment optimization algorithm has been developed based on typical polyenergetic proton beams generated from a typical laser proton accelerator and actual patient anatomy. Commonly used "inverse-planning" techniques include computer simulated annealing, iterative methods, filtered back projection and direct Fourier transformation. Considering the calculation time and the possible complexity with proton beams, the iterative optimization approach (based on a gradient search) is suitably adopted. This is based on iterative optimization algorithms for photon and electron energy- and intensity-modulation. Improved algorithms for energy- and intensity-modulated proton beams are tested. Further improvements of the algorithm is carried out in view of the special features of the realistic proton beams. The "optimizer" performs the following tasks: (1) takes the beamlet dose distributions from the dose calculation algorithm (see above), (2) adjusts the beamlet weights (intensities) to produce the best possible treatment plan based on the target/critical structure dose prescriptions, and (3) outputs the intensity maps (beamlet weighting factors) for all the beam ports and gantry angles for beam delivery sequence studies.

In accordance with an embodiment of the invention, a method of treating a patient includes the steps of identifying the position of a targeted region in a patient, determining the treatment strategy of the targeted region, the treatment strategy comprising determining the dose distributions of a plurality of therapeutically suitable high energy polyenergetic positive ion beams for irradiating the targeted region (e.g., determining the energy distribution, intensity and direction of a plurality of therapeutically suitable high energy polyenergetic positive ion beams); forming the plurality of therapeutically suitable high energy polyenergetic positive ion beams from a plurality of high energy polyenergetic positive ions, the high energy polyenergetic positive ions being spatially separated based on energy level using a superconducting electromagnet; and delivering the plurality of therapeutically suitable polyenergetic positive ion beams to the targeted region according to the treatment strategy.

In a related invention to the ion therapy system, the laser-accelerated high energy polyenergetic positive ion therapy system as described above in various embodiments can form the basis of a laser-accelerated high energy polyenergetic positive ion beam treatment center. In a laser-accelerated high energy polyenergetic positive ion beam treatment center, there is provided a main laser beam line that is reflectively transported using a series of beam reflectors, e.g., mirrors, to a target and ion selection system. The target and ion selection system includes the target system for generating high energy polyenergetic ions and an ion separation system. In one embodiment, the proton beam exiting the target and ion selection system includes therapeutically suitable high energy polyenergetic positive ions that are generated as described above. In this embodiment, the proton beam exiting the target and ion selection system are directed in the direction parallel to the direction of the laser beam entering the target and ion selection system. The ion beam in the treatment center is directed towards a couch, which locates the patient and the patient's target. In certain embodiments, the mirrors and target and ion selection system are capable of being rotated, for instance in the x-z plane, with the z direction being perpendicular to the x-y plane, around the axis of the main laser beam line using a gantry. In some embodiments, the final mirror from which the laser beam is reflected into the target and ion selection system is fixed to the target and ion selection system. The distance between the final mirror and mirror and ion selection system is shown adjustable along the y direction to permit scanning of the ion beam along the y direction.

Suitable target and ion selection systems are compact (i.e., less than about 100 to 200 kg in total mass, and less than about 1 meter in dimension, and incorporating superconducting electromagnets). The compactness of the target and ion selection systems permit their positioning with robotically-controlled systems to provide rapid scanning of the ion beam up to about 10 cm/s.

In one embodiment, treatment centers can use a proton ion beam. But treatment centers using other positive ions are also envisioned. Embodiments directed towards treatment centers using other light ions, for example lithium, beryllium, boron, or carbon, or any combination thereof, are also envisioned. The high energy polyenergetic positive ions typically have energy levels of at least about 50 MeV. These high energy polyenergetic positive ions are spatially separated based on energy level using superconducting electromagnets which are capable of providing a magnetic field of between about 0.1 and about 30 Tesla. In further embodiments, the magnetic field can be between about 0.2 and about 20 Tesla, about 0.5 and about 10 Tesla, or about 0.8 and about 5 Tesla.

In other embodiments of a laser-accelerated high energy polyenergetic positive ion beam treatment center, the center includes at least one of the ion therapy systems described above and at least one location for securing a patient, for example a couch. For example, a suitable treatment center of this type includes a laser beam that is reflectively transported to the target assembly using a plurality of mirrors. This treatment center can further include an optical monitoring and control system for the laser beam. Further embodiments include at least one beam splitter or mirror that is provided to split the laser beam into split or reflected laser beams to each of at least two target assemblies or to reflect the laser beam to one of the target assemblies. A suitable treatment center can have, for example, a laser-targeting system having two target assemblies and two ion selection systems each capable of individually producing a therapeutically suitable high energy polyenergetic positive ion beam from each of the individual high energy polyenergetic positive ion beams. Other embodiments can contain additional target assemblies and ion selection systems. An individual polyenergetic ion beam monitoring and control system is also provided for each of the therapeutically suitable high energy polyenergetic positive ion beams. One embodiment may include a mirror that is capable of being positioned in and out of the main laser beam to direct the beam to one of the ion therapy systems. Alternatively, a beam splitter can be used when a sufficiently powerful laser beam is provided so that split beams can be used simultaneously by two or more ion therapy systems. For providing patient privacy, typical ion therapy centers having two or more ion therapy systems will have an individual treatment room for each of the ion therapy systems. In such embodiments, the laser beam source is suitably located in a separate room or building. In embodiments with an optical monitoring system, the operator can know, and control, which of the ion therapy systems is being activated.

One embodiment of the high energy polyenergetic positive ion beam radiation treatment centers of the present invention also includes a suitable laser and a system for monitoring and controlling the therapeutically suitable high energy polyenergetic positive ions. Suitable lasers are typically housed in a building, such as in the same building as the positive ion beam treatment center, or possibly in a nearby building connected by a conduit for containing the laser beam. The main laser beam line is typically transported through the building within shielded vacuum conduit using a series of mirrors to direct the laser beam to the target and ion selection system. The target and ion selection system is typically mounted on a gantry, which is placed in a treatment room. In additional embodiments of the present invention, the main laser beam is split using a beam splitter into a plurality of laser beams emanating from a single laser. Each of the laser beams emanating from the beam splitter is directed to an individual target and ion selection system for treating a patient. In this fashion, high energy polyenergetic positive ion radiation treatment centers are provided using one laser source and a plurality of ion therapy systems to treat a plurality of patients. In certain embodiments of the high energy polyenergetic positive ion radiation treatment centers of the present invention, there are provided a plurality of treatment rooms, each treatment room having an individual target and ion selection system, a location for a patient, and a proton beam monitoring and controlling system. A plurality of treatment rooms equipped this way enables a greater number of patients that can be treated with the investment of one high power laser for providing therapeutically suitable high energy polyenergetic positive ions.

EXAMPLES AND OTHER ILLUSTRATIVE EMBODIMENTS

Figure 1:
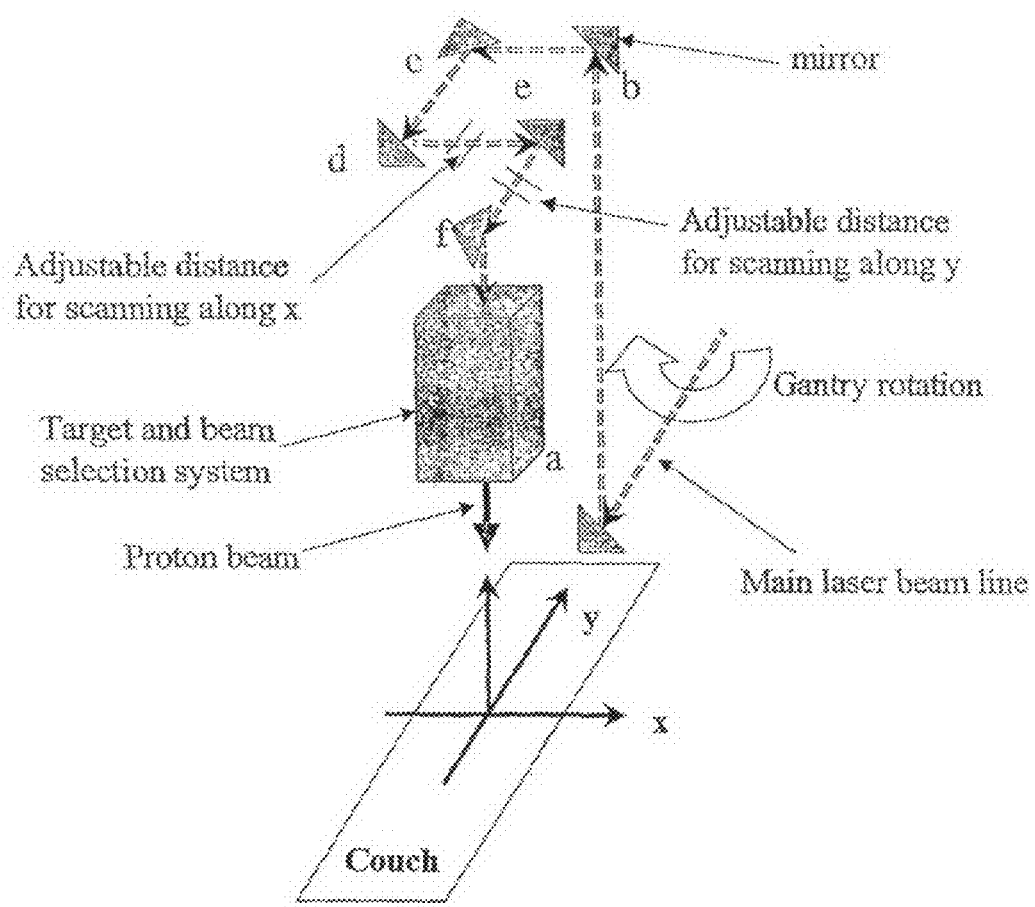
FIG. 1 is a schematic diagram of a laser-proton therapy unit.

Particle selection mechanism for a laser-proton accelerator. A laser-accelerated proton therapy system uses high intensity laser pulses to generate plasmas in a high density material, and accelerate the protons to high kinetic energies. One embodiment of a system design is shown in FIG. 1. The laser beam produced by a table-top-scale laser system (not drawn) is sent to the treatment unit through vacuum beam pipelines. The target assembly and the particle selection device is placed in the rotating gantry (not drawn). The laser beam is guided by a system of mirrors (a-e) as shown. The distances between mirrors are adjusted to scan the proton beam along the y- and z-axes and to generate a parallel scan beam. Alternatively, the target and the particle selection device are moved about the laser beam to achieve a parallel scan pattern.

A compact particle selection and beam collimation device is used to deliver small pencil beams of protons of different energies and intensities, as schematically described in one embodiment in FIG. 2. The particles produced by the laser include not just protons, but may also include various unwanted species such as photons, neutrons, and electrons. The protons coming from the target are mainly accelerated forward along the x-axis, which can be the beam axis. A step magnetic field, (see, e.g., FIG. 3) distributed in four separated regions, can be used to deflect protons and electrons. In the first region (a), the magnetic field points into the plane or −z-direction, and the protons are pushed up. When they enter into the second (b) and the third (c) region, the field is flipped to the z-direction, and the protons are pulled down. The field in the last region (d) puts the protons back to the original beam axis. As shown in FIG. 2 a beam stopper can be placed on the beam axis to block the photons and neutrons as well as high energy protons. The electrons are deflected downward by the magnetic field and are absorbed by an electron stopper placed in the lower part of the device. Other unwanted particles missed by the stoppers can be absorbed by the shielding surrounding the particle selection device.

The deflection of protons depends on the proton energy. The protons with low energies are more deflected than those with high energies. Thus, particles with different energies are spatially separated in the y-direction. A collimator aperture is placed near the center of the system at certain position on the y-axis, where the protons of given energy pass through its opening; the particles with other energies are stopped by the collimator. In one embodiment, two more collimators are used to control proton beam size; one is at the beginning of the magnetic field (primary collimator), and the other (secondary collimator) is at the end. A non-step magnetic field can be used to model the performance of this embodiment of the present invention.

Calculation of the magnetic field produced by rectangular loops. A strong magnetic field can be generated by a cylindrical winding of conventional metal wire, and preferably superconducting wire. The calculation of the complete field distribution is electromagnet dependent and very complicated. Analytical solutions can be quite difficult to obtain, except for very few special points. A superconducting electromagnet can be treated as a stack of current loops. An analytical calculation of magnetic field distribution for a single rectangular loop can be performed using the Biot-Savart law. Thus, a complete 3-D field distribution for the superconducting electromagnet can be obtained by summing up the fields for each loop.

Figure 4:
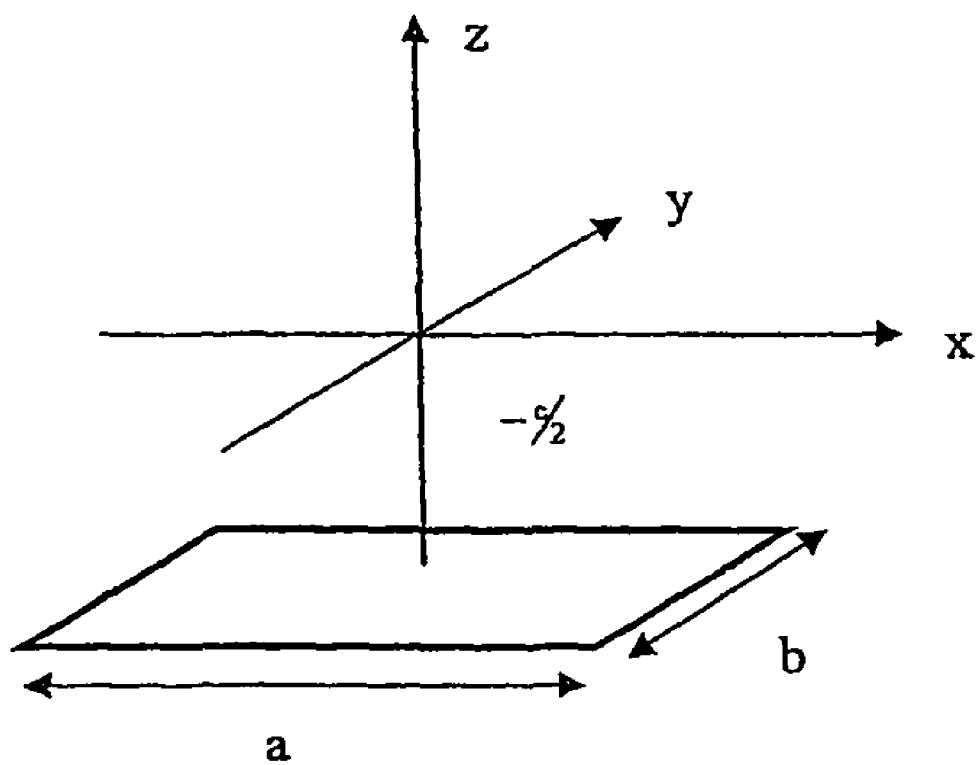
FIG. 4 depicts a rectangular loop located at $z=-c/2$. The length in the x-axis is a, while it is b in the y-axis.

A single rectangular loop carrying a current I is shown in FIG. 4, and the three components of the magnetic field strength, $B_x$, $B_y$, $B_z$, are analytically calculated and given in the Appendix, below.

The field for multiple loops is the superposition of the fields for individual loops.

$$B_{x,y,z} = \sum_{i=1}^{n} B_{x,y,z}((i-1)\Delta z + z_1), \tag{1}$$

where $\Delta z$ is the distance between two adjacent loops, $z_1$ the position of the first loop, and n the total number of loops. The electromagnet coil can be treated as multiple current loops assuming the uniform current density in the coil.

Figure 5:
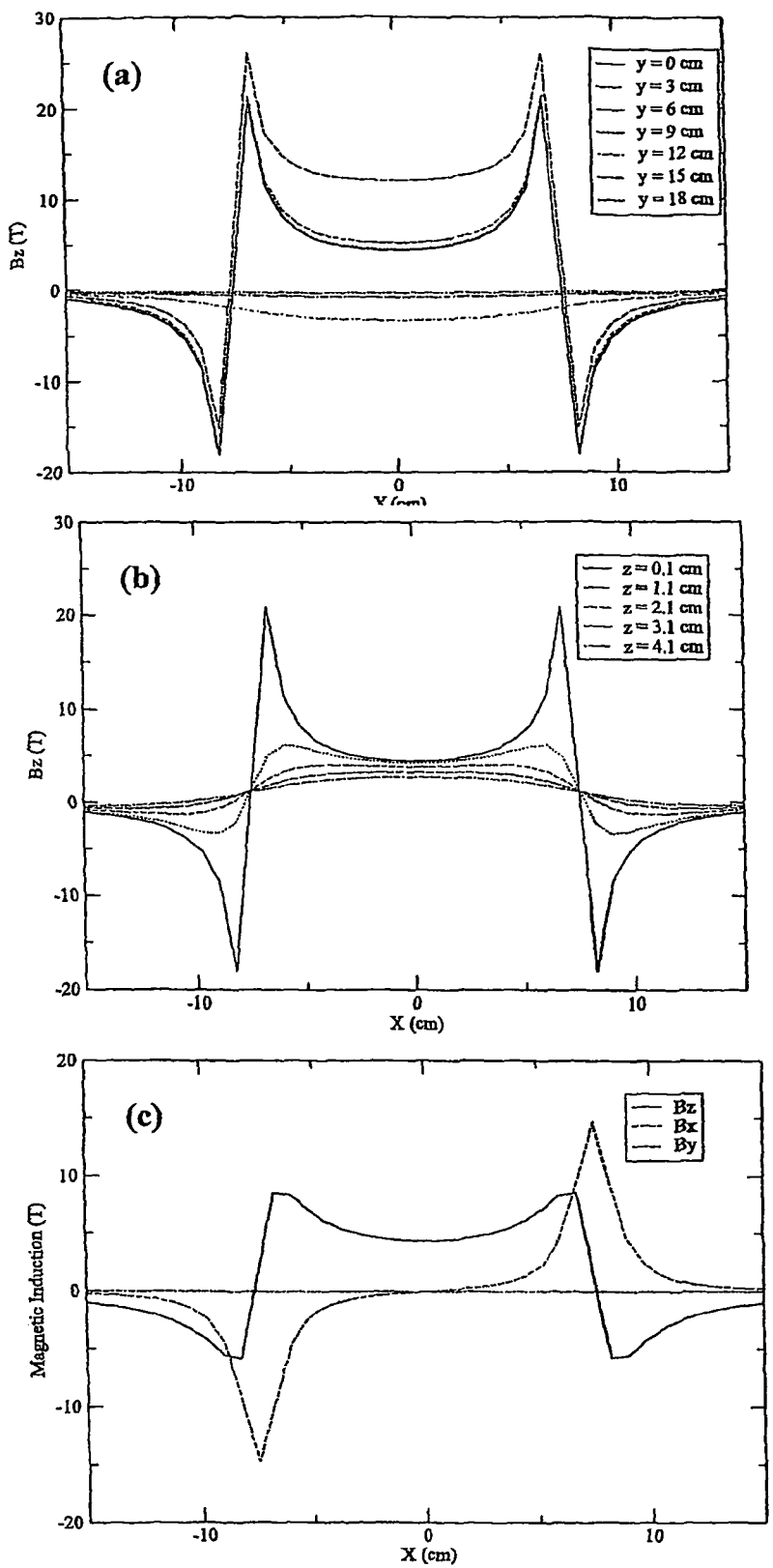
FIG. 5 shows field distributions for a single loop shown in FIG. 4, whose size is defined by $a=15$ cm (x-axis) and $b=30$ cm (y-axis): (a) $B_z$ at $z=0.1$ cm for different positions in the y-axis; (b) $B_z$ at $y=0$ cm for different positions in the z-axis; and (c) a comparison between $B_x$, $B_z$, $B_z$ at $y=1$ cm, $z=1$ cm.

A computer code was written to simulate the magnetic field of the rectangular loop based on the calculation. The field distribution along the x-axis or the beam axis for the single loop is plotted in FIG. 5. As can be seen, $B_z$ is not uniformly distributed in the x-axis. Two peaks appear at the edge of the loop. Also, $B_z$ has big variation in either the y- or z-directions as shown in FIGS. 5 (*a*) and (*b*). A comparison among the three components of the field in (c) shows that $B_x$ dominates over $B_z$ at the edges of the loop and will significantly change the total field around the edges, while $B_y$ can be ignored. Thus, more than one loop can be used to produce a uniform magnetic field.

Another loop with the same size and current in parallel along the z-axis can be added. This is similar to the circular Helmhotz coil. The distance between the two loops in this example is about 4 cm. The field distribution for the double loop is not much different from the distribution of the single loop. The peaks are still present, although the peaks of $B_x$ have been somewhat reduced. This indicates that adding loops in the z-direction can reduce the peaks and flatten out the field distribution.

Figure 6:
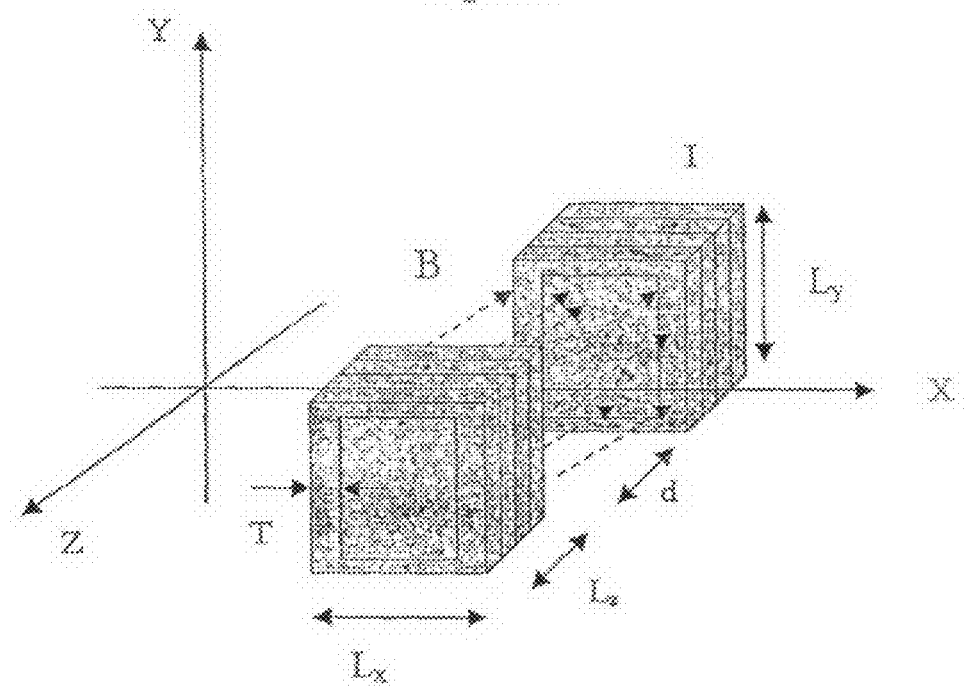
FIG. 6 is a schematic description of a multi-coil superconducting electromagnet. 2×10000 turns of NbTi wire carries a current, I=85 A, and produces a magnetic field, B=4.4 T at 4.2 K. $L_x=15$ cm, $L_y=30$ cm, $L_z=20$ cm, and T=0.2 cm.

Superconducting Electromagnet Embodiments. As mentioned above, more loops can be used to stack vertically along the z-axis to reduce the peaks and smooth the field distribution. Loops can be stacked to make electromagnets; a superconducting electromagnet can be made by winding a long wire by multiple turns that are magnetically equivalent to a stack of loops as shown in FIG. 6. Two such superconducting electromagnets can be connected together, which provide a gap, d, between, where a somewhat uniform magnetic field is provided and protons will pass therethrough. The dimensions of a single superconducting electromagnet can be determined with both the laser-proton system design and the selection of the material of the wire in mind. A compact laser-proton system can include a compact electromagnet system. In one embodiment of the present invention, the upper limit on the dimensions of a single superconducting electromagnet is set to about $20 \times 40 \times 25$ cm$^3$ ($L_x \times L_y \times L_z$). As used herein, the mathematical symbol tilde ("~") used in front of a number means "about". If a conventional copper wire is used, which can carry a current with a density of ~$10^3$ A/cm$^2$, the cross section of the electromagnet coil wound with the copper wire should be ~$10^3$ cm$^2$ to get a total current of ~$10^6$ A to achieve a magnetic induction of ~4.4 T (see Appendix). Thus, a thickness (T) of about 40 cm for a conventional non-superconducting electromagnet with a length ($L_z$) of about 25 cm can be used to meet the cross section, which makes the width in both x- ($L_x$) and y-direction, ($L_y$) much greater than about 80 cm. While such electromagnets can be used in the present invention, it is desirable to use even smaller electromagnets.

Figure 7:
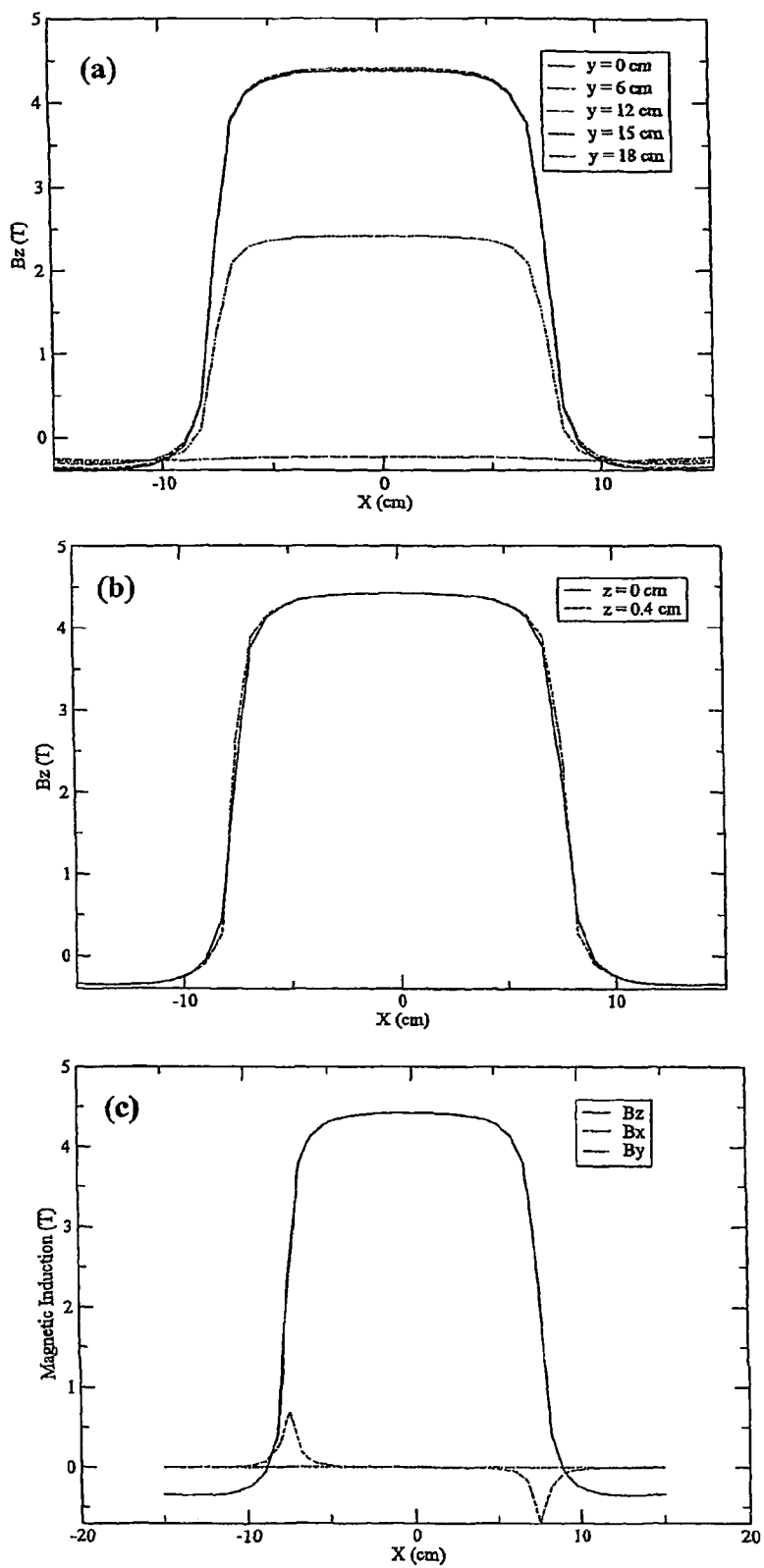
FIG. 7 depicts field distributions for a pair of superconducting electromagnets with $L_x$ 15 cm, $L_y=30$ cm, and $L_z=20$ cm. The gap between the electromagnets along the z-axis is 1 cm: (a) $B_z$ for different y at $z=0.2$ cm; (b) $B_z$ for different z at $y=7.5$ cm; and (c) a comparison between $B_x$, $B_z$, $B_z$ at $y=7.5$ cm, $z=0.2$ cm.

The size of the electromagnet can be significantly reduced by utilizing superconducting wires instead of copper because a superconducting wire can carry a very high current density. Another advantage of using superconducting wires is saving power. The power consumption for a superconducting electromagnet is only about 1% to about 10% of that for a comparable conventional electromagnet. Superconducting wires are commercially available and have been widely used in high energy accelerators to produce strong magnetic fields. A suitable superconducting wire is NbTi, which has a critical current density of ~$4.25 \times 10^5$ A/cm$^2$ at 4.2 K for a field of ~4.4 T. Another commercially available superconducting wire, Nb$_3$Sn, can also be used. Other types of superconducting wires, including those made from high temperature superconductors, can be used. Suitable high temperature superconducting wires are commercially available from the American Superconductor, Westborough, Mass. (http://www.amsuper.com/index.cfm). Suitable superconducting wires, such as NbTi wire, is commercially available in widths of from about 10 micron to 250 micron diameter form Japan Superconducting Technology, Inc. Tokyo, Japan, (http://www.jastec.org/eg/index.html). The actual current can be less than the critical current, otherwise, the superconducting state can be broken and the wire will function in the conventional conducting state. In one embodiment, to generate a magnetic field of ~4.4 T, a suitable super-conducting wire, such as NbTi wire of about 0.2 mm in diameter, which carries a current of about 85 A, is wound 10000 turns to make a rectangular superconducting electromagnet of about 20 cm in length ($L_z$) and about 0.2 cm in thickness. Thus, a pair of such superconducting electromagnets will be about 40 cm long, including a gap (d) of about 1 cm. The coil cross section in the superconducting electromagnet is about 20 cm $\times$0.2 cm, so the current density is only about $2 \times 10^5$ A/cm$^2$, which is less than the critical current density and therefore can be used for maintaining the superconductivity. As a result, the electromagnet size can be reduced by a factor of ~200 using superconducting wires. Suitable superconducting wires can have a thickness in the range of from about 10 nanometers ("nm") to about 5 mm. In one embodiment, suitable superconducting wires can have a thickness of about 0.2 cm, and are coiled in a rectangular fashion to provide dimensions of width of about 15 cm in the x-axis, and a width of about 20 cm in the y-axis. Such superconducting electromagnets are suitable and produce a smooth magnetic field, as shown in FIG. 7. The edge peaks of $B_z$ are substantially removed and $B_x$ has only small peaks at the edges.

Figure 3:
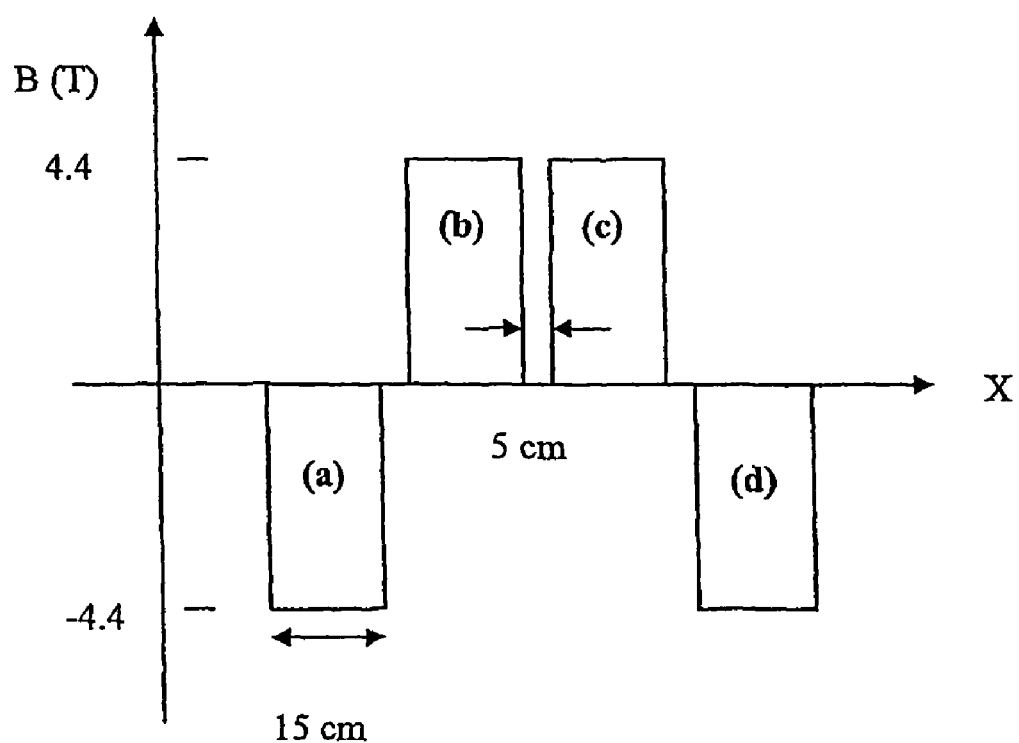
FIG. 3 depicts an ideal step field used for particle selection.

In one embodiment, four electromagnets are used to achieve a step-like field distribution (see FIG. 3). The electromagnets are placed parallel along the x-axis (beam axis) with the first and the fourth electromagnet field pointing to $-z$, and the second and third magnetic field pointing to z. The first electromagnet produces the magnetic field with the Lorentz force that pushes protons up, then the second and the third produce the field that pulls the protons down, and the field from the last one puts the protons back to the original direction. This superconducting electromagnet system only takes about 80 cm along the beam axis, which is comparable in size to a photon and electron accelerator. A smooth step-like field distribution (see FIG. 8) is produced with I=85 A and $B = B_z \sim 4.4$ T. $B_x$ and $B_y$ are small and can be ignored. In this embodiment $B \approx B_z$.

The following description is directed to the dynamics of protons, as one illustrative embodiment Additional embodiments directed to other positive ions in addition to protons are also envisioned. Other embodiments directed towards lithium, beryllium, boron, carbon, or other light ions, or any combination thereof are also envisioned.

Proton transport and optimization of the electromagnet system. One embodiment of the superconducting electromagnet system of the present invention can be tested by studying proton transport in the magnetic field produced by the system. The magnetic field can separate protons with different energies in their trajectories and returns substantially all of the desired protons moving initially along the beam axis to the beam axis. The proton's dynamics can be described by the equation of motion $$\frac{dp}{dt} = qv \times B \qquad (2)$$

where p is the momentum of the proton, q is the charge of the proton, and v is the velocity of the proton. Based on a symplectic algorithm, a simulation code has been written to give a numerical solution for proton trajectories. A number of factors are discussed, which can influence the field distribution and affect the proton beams. Those parameters can be fine tuned to optimize a electromagnet system.

Beam collimation. In this embodiment, a PIC simulation has shown that, for the given laser-plasma parameters, the protons can have an energy spectrum that is much wider than needed in clinical applications. Collimators can be introduced to block or slow the unwanted protons and collimate the desired particle beams. In the proton collimation, the beam size and its energy spread can be considered. The beam size can be selected by the treatment plan, and determined by the primary collimator in the beginning and the secondary collimator in the end. For instance, for intensity modulated proton therapy, a pencil beam with a 1×1 cm² field at SSD of 100 cm can be used. The primary collimator opening is usually not arbitrarily large, since it directly controls the energy spread of the resultant beam. The primary collimator aperture can be chosen in various embodiments of the present invention to be such that particles that subtend an angle of about 2*arctan(0.025/5.0) are permitted to go through, thus giving a beam size of about 1×1 cm² at about 100 cm SSD.

Figure 9:
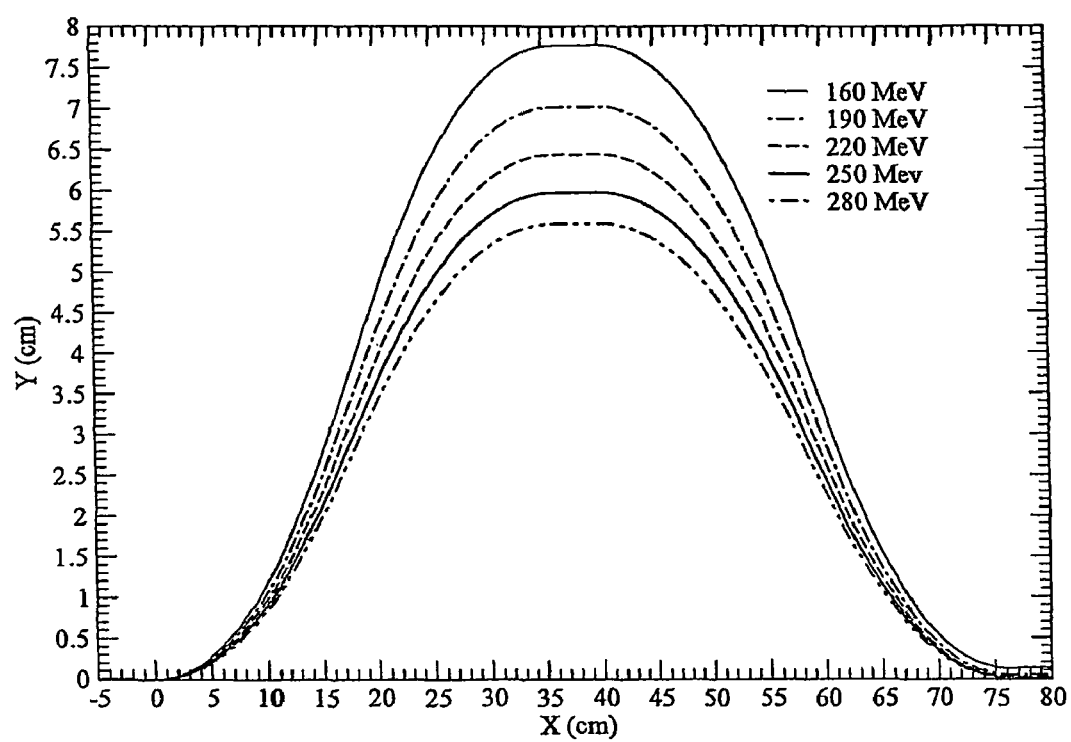
FIG. 9 depicts trajectories of protons for different kinetic energies. The distance between 250-MeV protons and 220-MeV protons is about 0.46 cm in the middle of the particle selection system while the distance between the 190- and 160-MeV protons is about 0.8 cm.

In one embodiment, the middle collimator is used to shape the energy spectrum of the spread out protons to obtain clinically useful beams. The results in FIG. 9 show that a 0.40-cm aperture opening can be used to collect substantially all 250-MeV particles with a less than 30 MeV energy spread, not accounting for the angular distribution. Considering that the protons have an inherent angular spread originating from the laser interaction with the solid structure, more divergent proton beams and broader energy spread for each beam can arise for similar collimation parameters given above. Thus, the aperture size can be slightly reduced to control the energy spread in the beam. An about 0.3-cm aperture has been used in the following embodiment. A secondary collimator is also introduced in this embodiment to establish a suitable beam size and filter out remaining unwanted particles.

Figure 10:
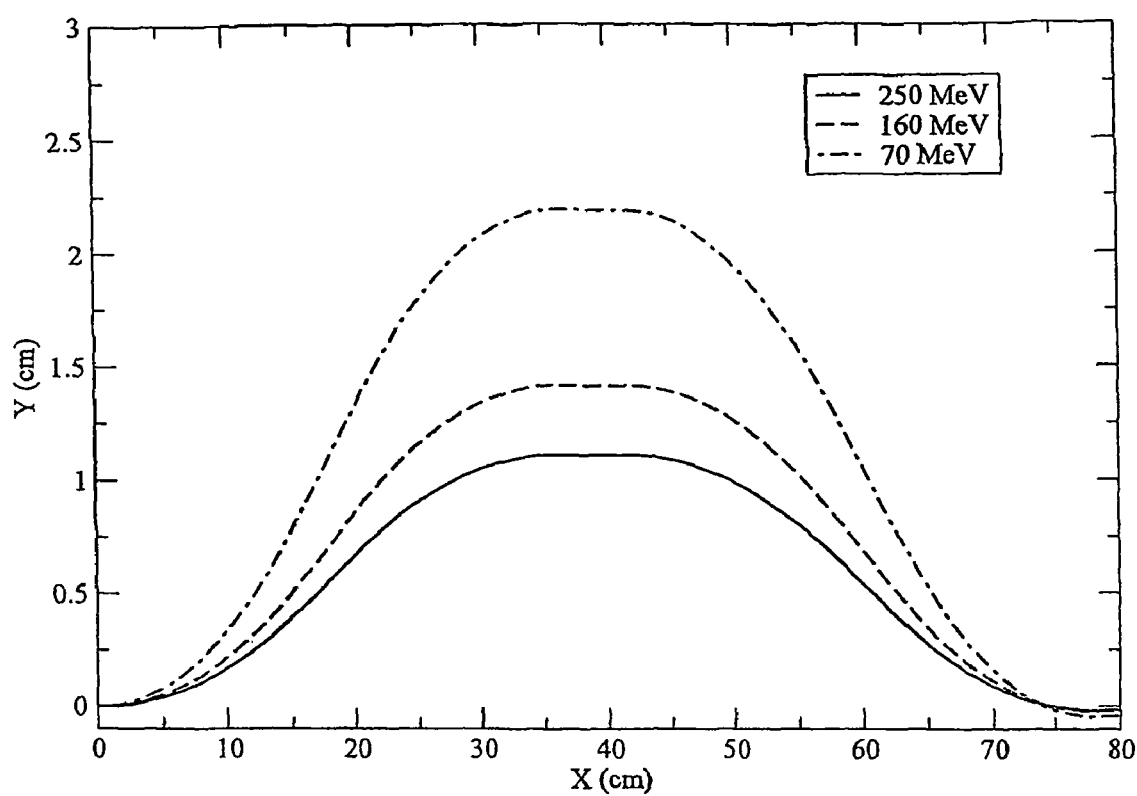
FIG. 10 depicts proton trajectories for B=0.8 T.

Field strength. In this embodiment, the maximum deviation of the proton beam from the central axis $y_m$ can increase with the magnetic field strength B. This deviation can determine the size of the selection system. The spatial separation of two proton beams with adjacent characteristic energies at the point of their maximum deviation $y_m$ can be related to the deviation itself, as shown in FIG. 9. The lower $y_m$ can result in the smaller spatial separation, thus larger resultant energy spread in the proton beam. Maintaining a reasonably small energy spread can be established by using a small value of $y_m$. The absolute value of the magnetic field is usually not too small. FIG. 10 shows the effect of the magnetic field strength. For a small field of 0.8 T, the electromagnet width in the y-axis can be reduced to less than 2.5 cm, but the energy spread for protons with characteristic energy higher than 160 MeV can be too large to be acceptable as shown in FIG. 14(b). These results indicate that a field strength of about B=4.4 T and a electromagnet width in the y-direction of about $L_y$=20 cm provides a suitable compact selection system with acceptable energy spread in the final proton beam.

Figure 11:
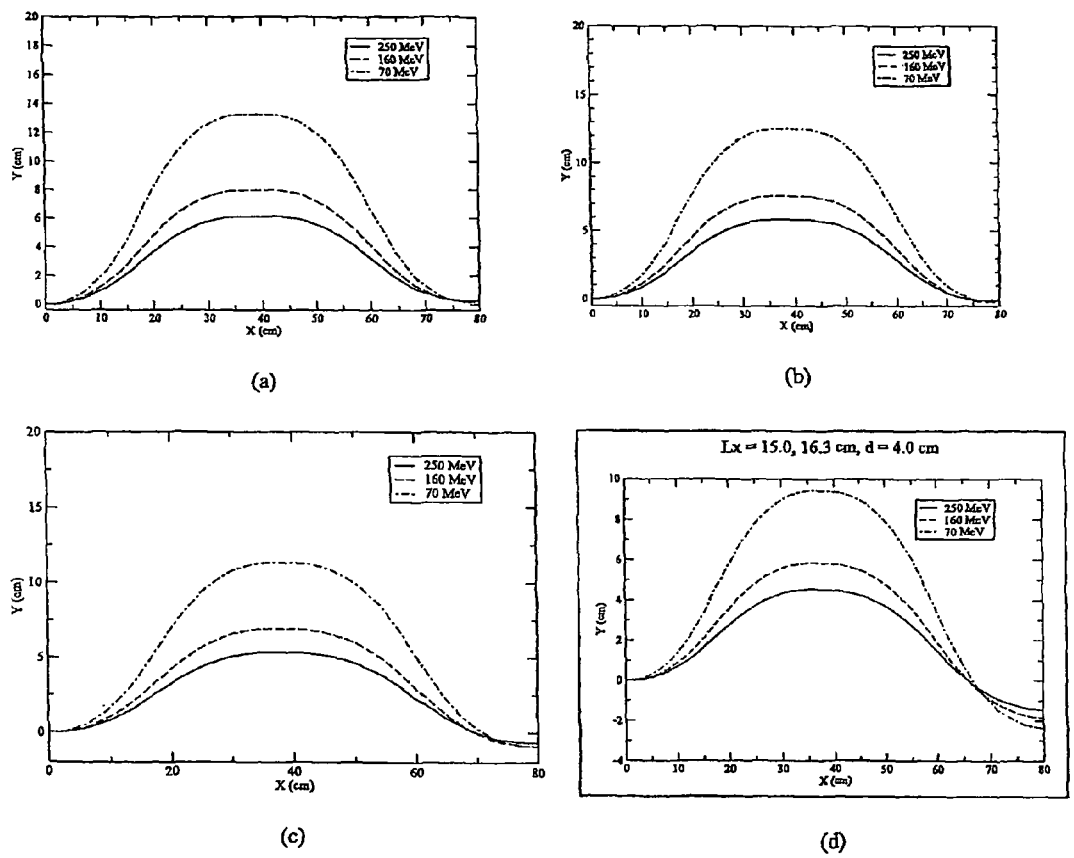
FIG. 11 depicts proton trajectories for a different gap, d, where the width for the middle electromagnets is $L_x=16.3$ cm: (a) d=0.5 cm. (b) d=1.0 cm. (c) d=2.0 cm. (d) d=4.0 cm.

Gap between the paired electromagnets. In certain embodiments, the protons traversing the magnetic field can refocus on the beam axis where the secondary collimator is placed. However, since the magnetic field is not always step-distributed, the y-position of the protons at the secondary collimator, $y_s$, can deviate from 0. In certain embodiments, $y_s$ can be affected by the field strength and the field shape, both of which are related to the gap between the two paired superconducting electromagnets. Usually, $y_s$ varies with different energies. Thus, the secondary collimator can be moved along the y-axis to collect the proton beams with different energies. However, the position of the secondary collimator is usually fixed for all energies in order to avoid the uncertainties caused by moving the collimator. In order to achieve this, the gap can be tuned to shape the field in such a way as to allow the required protons with different energies to focus on the same point $y_s$, which is close to 0. FIG. 11 shows the trajectories of a proton for d=0.5, 1, 2, 4 cm. For d=1.0 cm, the difference of $y_s$ for different energies is minimum and the closest to zero, thus, a 1.0-cm gap is used in certain embodiments of the invention.

Figure 8:
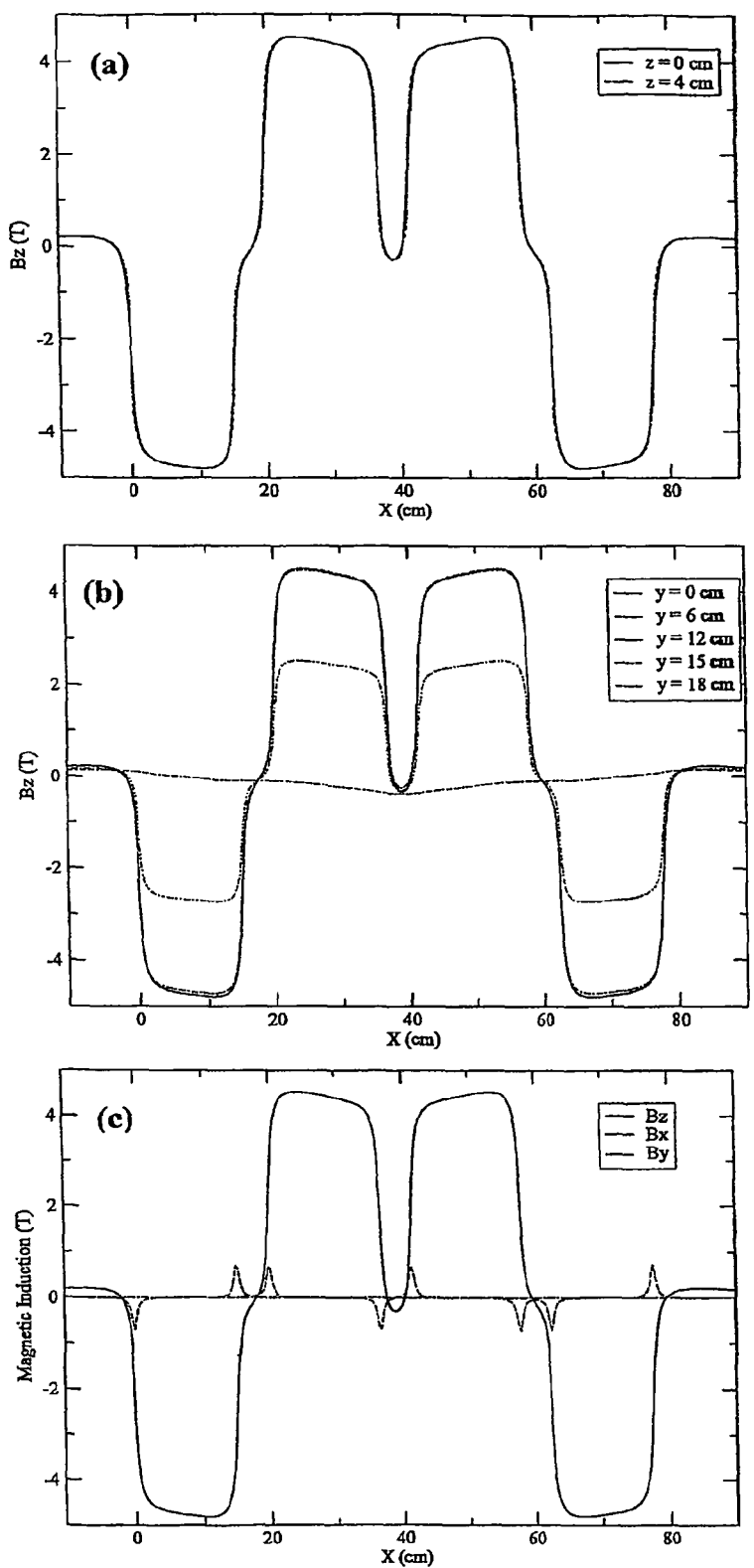
FIG. 8 depicts field distributions from a 4-electromagnet system: (a) Bz for different z at $y=7.5$ cm. The field does not change much in the z-direction. (b) Bz for different y at $z=0.2$ cm. The field does not change much in the y-direction for y less than 15 cm within the electromagnet region. (c) A comparison between $B_x$, $B_z$, $B_z$ at $y=7.5$ cm, $z=0.2$ cm.

Width of the middle electromagnets. In certain embodiments, the trajectories of the protons can be very sensitive to the width of the middle electromagnets in the x-direction (i.e., the beam direction), $L_x$. In an alternate variation, the width for all four electromagnets was set as 15 cm to be consistent with the step field distribution. With this configuration, the protons usually did not return to the x-axis and diverge at x=80 cm for different energies as shown in FIG. 12 (a). Using 17 cm in a different variation also led to protons not returning to the x-axis, as shown in FIG. 12(b). Without being bound to a specific theory of operation, it is believed that the protons are not returning to the x-axis because the field strength for the second and third electromagnet is lower than that for the first and fourth, as shown in FIG. 8. These examples show that $L_x$=16.3 cm leads to the best results in this embodiment (see FIG. 11(b)).

These results show that the importance of the design parameters of a suitable electromagnet system for a polyenergetic positive ion beam selection device for use in laser-accelerated proton beam therapy. The parameters of the electromagnet system are readily determined with the system design and the simulation of proton transport, as provided in the various aspects of the present invention.

Figure 13:
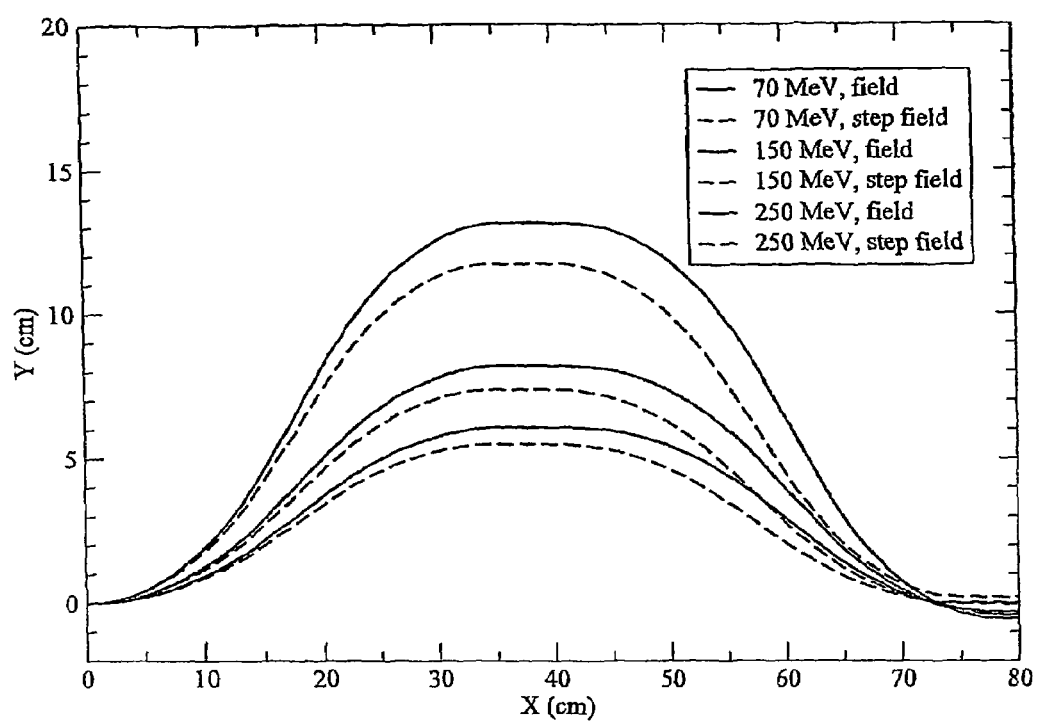
FIG. 13 is a comparison of proton trajectories between the ideal field (corresponding to dashed lines) and electromagnet-produced field (corresponding to solid lines). Lower energy proton trajectories towards the top (higher y values); higher energy proton trajectories towards the bottom (lower y values).

FIG. 13 compares the proton trajectories in the electromagnet-generated field and the ideal step field. The trajectories in the former case are shifted up in the y-direction. This appears to result from the field strength in the first and the fourth region being larger than that in the middle to balance the asymmetry of the field distribution, while the field strength for all four regions is the same in the latter case.

Energy spectrum and dose distribution. Without being bound by any particular theory of operation, it is believed that the energy spread of a proton beam comes from the broad energy and angular distribution of the laser-accelerated protons. The resulting polyenergetic proton beams are clinically useful for irradiating tumors. With an ideal step magnetic field, preliminary results have shown that although each polyenergetic laser-accelerated proton beam results in a less sharp depth-dose falloff, nonetheless it can be combined and modulated to generate a spread-out Bragg peak (SOBP) with a well-conformal coverage of the target. The energy spectra and the corresponding dose distributions can be recalculated in the presence of the magnetic field produced by a superconducting electromagnet system of the present invention.

Figure 14:
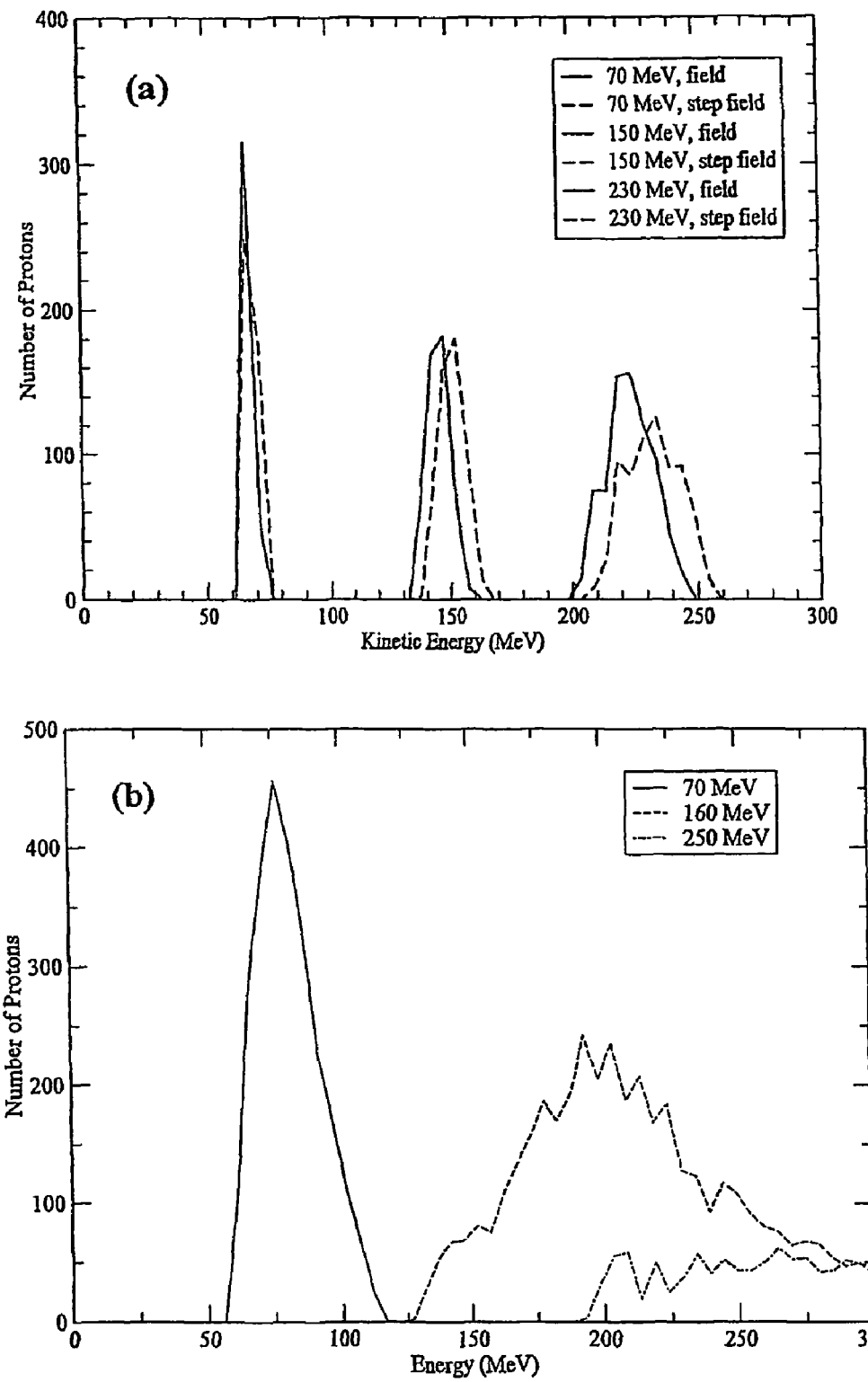
FIG. 14 depicts energy spectra for selected energies: (a) The spectra for the electromagnet-generated field and step field. B=4.4 T. (b) The spectra only for the electromagnet-generated field. B=0.8 T.

To calculate the energy spread centered around the characteristic energy E, $y_m(E)$, the y-position of the proton with energy E, when the proton reaches $x_m$, the x-position where the particle selection aperture is placed is determined. Then, the aperture center is moved to $y_m(E)$, with a width of 3 mm, and the protons which pass through the aperture are counted. Thus, a proton beam with an energy spread peaked around E is obtained. The energy spectra for three beams are shown in FIG. 14. Lower energy proton beams have smaller energy spread in their distributions, whereas the high energy beams have larger energy spread. Without being bound by a particular theory of operation, this result is apparently due to the fact that the higher energy protons are less deflected by the magnetic field and thus are less divergent than the lower energy protons. FIG. 14(b) shows the energy spread increases with the decrease of the field strength. For B=0.8 T, the energy spread is larger than 100 MeV for the characteristic energy higher than 160 MeV. This energy spread is not optimally desirable for certain embodiments of the invention.

The dose distributions for the polyenergetic proton beams can be calculated using the GEANT3 Monte Carlo code. Since the energy spread tends to spread out the Bragg peak, the wider energy distribution typically gives rise to a flatter Bragg peak, as is shown in FIG. 15.

Figure 15:
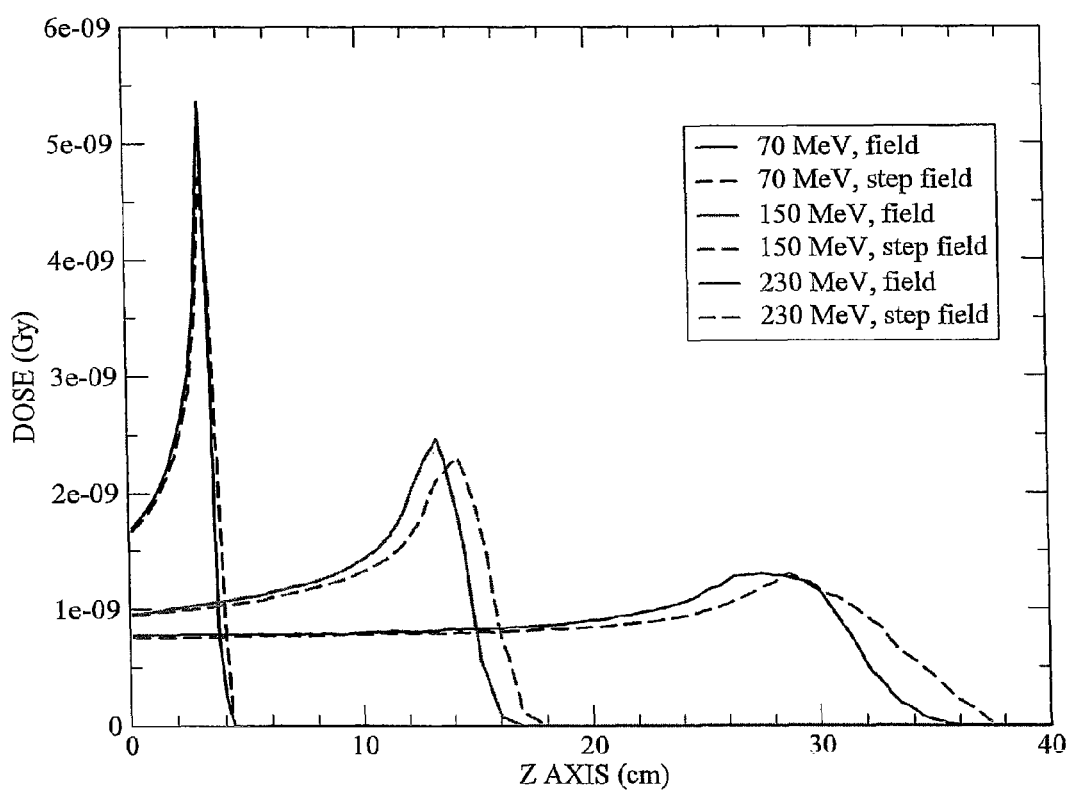
FIG. 15 depicts dose distributions for the proton beams selected at different energies. Solid lines represent using the electromagnet-generated field and the dashed lines represent using an ideal step field.

FIGS. 14 and 15 compare the energy spectra and associated depth-dose distributions calculated using the ideal step magnetic field distribution and that for the electromagnet-produced system. The proton energy spectra for the electromagnet-generated field are somewhat shifted to lower energy regions, which appears to be consistent with FIG. 13.

One embodiment of the invention provides a compact superconducting electromagnet system capable of producing a step-like magnetic field distribution, which is useful for proton beam selection. One design of the superconducting electromagnet system is obtained from the analytical calculation of the magnetic field for rectangular coils, which provides a three dimensional magnetic field distribution, thus accounting for such boundary effects as edge focusing due to the influence of the fringing field patterns at the edge of the coils. The simulation of proton trajectories is used to test the electromagnet system and optimize the design for certain criteria.

These results indicate that clinically acceptable quality proton beams can be produced with an embodiment of a suitable magnetic selection system using the following parameters: The dimensions of a single electromagnet can be about $L_x$=15 cm (outer), 16 cm (inner), $L_y$=30 cm, and $L_z$=20 cm. An average magnetic induction of about 4 to 5 T, is provided using a loop current of about I=85 A with about 10000 turns of a suitable superconducting wire, such as NbTi wire. The current can vary between 60 A and 600 A depending on the fabrication of superconducting wires and the use of power supply. The gap between the paired electromagnets can be about 1 cm The aperture size for the three collimators can be set to about 0.05 cm for the primary, 0.3 cm for the selection aperture, and 0.8 cm for the secondary.

Using the electromagnet system of this embodiment, energy spectra are obtained for different selected characteristic energies. Compared with the energy spectra obtained with the ideal step field distribution, they have a small shift to low energy regions, but they both have almost the same spreads. This agrees with the dose distribution pattern obtained with those energy spectra.

The superconducting electromagnet systems of the present invention are useful in the particle selection mechanism of our related invention, International Patent Application No. PCT/US2004/017081, filed Jun. 2, 2004, entitled "High Energy Polyenergetic Ion Selection Systems, Ion Beam Therapy Systems, and Ion Beam Treatment Centers", the entirety of which is incorporated by reference herein. Accordingly, the superconducting electromagnet systems provided herein can be used for producing clinically usable proton beams. These systems can be modeled using Monte Carlo calculations of dose distributions based on real patient geometry.

APPENDIX

We apply the Biot-Savart law to the rectangular current loop shown in FIG. 4

$$B = \oint_C \frac{\mu_0 I dl \times r}{4\pi r^3} = \sum_{i=1}^{4} \int_{Li} \frac{\mu_0 I dl \times r_i}{4\pi r_i^3}, \quad (I)$$

where B is magnetic induction, $\mu_o$ the permeability of free space, which is equal to $4\pi \times 10^{-7}$ NA$^{-2}$. I is the current carried by the loop, and $r_i$ is the distance between the current element of the i-th side of the loop and the point (x, y, z) and given by:

$$r_i = ((x-x_i)^2 + (y-y_i)^2 + (z-z_i)^2)^{1/2}, \quad i=1,2,3,4.$$

Integrating Eq. (I) over the loop, we obtain the three components of the magnetic field $$B_x = -\frac{\mu_0 I(y-b/2)(z+c/2)}{4\pi[(x+a/2)^2 + (z+c/2)^2]} + \quad (II)$$
$$((x+a/2)^2 + (y-b/2)^2 + (z+c/2)^2)^{1/2}$$

$$\frac{\mu_0 I(y-b/2)(z+c/2)}{4\pi[(x-a/2)^2 + (z+c/2)^2]} +$$
$$((x-a/2)^2 + (y-b/2)^2 + (z+c/2)^2)^{1/2}$$

$$\frac{\mu_0 I(y+b/2)(z+c/2)}{4\pi[(x+a/2)^2 + (z+c/2)^2]} -$$
$$((x+a/2)^2 + (y+b/2)^2 + (z+c/2)^2)^{1/2}$$

$$\frac{\mu_0 I(y+b/2)(z+c/2)}{4\pi[(x-a/2)^2 + (z+c/2)^2]},$$
$$((x-a/2)^2 + (y+b/2)^2 + (z+c/2)^2)^{1/2}$$

$$B_y = \frac{\mu_0 I(x+a/2)(z+c/2)}{4\pi[(y+b/2)^2 + (z+c/2)^2]} - \quad (III)$$
$$((x+a/2)^2 + (y+b/2)^2 + (z+c/2)^2)^{1/2}$$

$$\frac{\mu_0 I(x+a/2)(z+c/2)}{4\pi[(y-b/2)^2 + (z+c/2)^2]} -$$
$$((x+a/2)^2 + (y-b/2)^2 + (z+c/2)^2)^{1/2}$$

$$\frac{\mu_0 I(x-a/2)(z+c/2)}{4\pi[(y+b/2)^2 + (z+c/2)^2]} +$$
$$((x-a/2)^2 + (y+b/2)^2 + (z+c/2)^2)^{1/2}$$

$$\frac{\mu_0 I(x-a/2)(z+c/2)}{4\pi[(y-b/2)^2 + (z+c/2)^2]},$$
$$((x+a/2)^2 + (y-b/2)^2 + (z+c/2)^2)^{1/2}$$

and

-continued $$B_z = \frac{\mu_0 I(x+a/2)(y+b/2)}{4\pi[(y+b/2)^2+(z+c/2)^2]} \cdot \frac{1}{((x+a/2)^2+(y+b/2)^2+(z+c/2)^2)^{1/2}} + \quad (IV)$$

$$\frac{\mu_0 I(x-a/2)(y-b/2)}{4\pi[(y-b/2)^2+(z+c/2)^2]} \cdot \frac{1}{((x-a/2)^2+(y-b/2)^2+(z+c/2)^2)^{1/2}} +$$

$$\frac{\mu_0 I(x-a/2)(y+b/2)}{4\pi[(y+b/2)^2+(z+c/2)^2]} \cdot \frac{1}{((x-a/2)^2+(y+b/2)^2+(z+c/2)^2)^{1/2}} -$$

$$\frac{\mu_0 I(x-a/2)(y-b/2)}{4\pi[(y-b/2)^2+(z+c/2)^2]} \cdot \frac{1}{((x-a/2)^2+(y-b/2)^2+(z+c/2)^2)^{1/2}} +$$

$$\frac{\mu_0 I(x+a/2)(y-b/2)}{4\pi[(x+a/2)^2+(z+c/2)^2]} \cdot \frac{1}{((x+a/2)^2+(y-b/2)^2+(z+c/2)^2)^{1/2}} -$$

$$\frac{\mu_0 I(x-a/2)(y-b/2)}{4\pi[(x-a/2)^2+(z+c/2)^2]} \cdot \frac{1}{((x-a/2)^2+(y-b/2)^2+(z+c/2)^2)^{1/2}} -$$

$$\frac{\mu_0 I(x+a/2)(y-b/2)}{4\pi[(x+a/2)^2+(z+c/2)^2]} \cdot \frac{1}{((x+a/2)^2+(y-b/2)^2+(z+c/2)^2)^{1/2}} +$$

$$\frac{\mu_0 I(x-a/2)(y+b/2)}{4\pi[(x-a/2)^2+(z+c/2)^2]} \cdot \frac{1}{((x-a/2)^2+(y+b/2)^2+(z+c/2)^2)^{1/2}}.$$

For a special point (0, 0, −c/2), the center of the loop, the z-component of the magnetic field is reduced to a known expression, (N. Ida and J. Baotos, Electromagnetics and Calculation of Fields, Springer-Verlag, 1992)

$$B_z = -\frac{2\mu_0 I}{\pi} \frac{\sqrt{a^2+b^2}}{ab}. \quad (V)$$

Eq. (V) can be used to estimate roughly what current is needed for a given magnetic field strength. For $B_z$=4.4 T, a=0.15 m, and b=0.3 m, the required current is $$I = \frac{\pi B_z}{2\mu_0} \frac{ab}{\sqrt{a^2+b^2}}$$

$$= \frac{\pi \times 4.4 \times 0.15 \times 0.3}{2 \times 4\pi \times 10^{-7} \sqrt{0.15^2+0.3^2}}$$

$$= 7.4 \times 10^5 \text{ A}.$$

Thus, in order to produce a field of ~4.4 T close to the plane of the loop, the current I has to be ~$10^6$ A.

What is claimed:

1. A method of treating a patient with a laser-accelerated high energy polyenergetic positive ion therapy system, comprising:
    identifying the position of a targeted region in a patient;
    determining the treatment strategy of the targeted region, said treatment strategy comprising determining the dose distributions of a plurality of therapeutically suitable high energy polyenergetic positive ion beams for irradiating the targeted region;
    forming said plurality of therapeutically suitable high energy polyenergetic positive ion beams from a plurality of high energy polyenergetic positive ions, that are spatially separated based on energy level using one or more superconducting electromagnets each capable of providing a magnetic field of between about 0.1 and about 30 Tesla; and
    delivering the plurality of therapeutically suitable polyenergetic positive ion beams to the targeted region according to the treatment strategy.

2. The method of treating a patient with a laser-accelerated high energy polyenergetic positive ion therapy system of claim 1, wherein the magnetic field is between about 0.2 and about 20 Tesla.

3. The method of treating a patient with a laser-accelerated high energy polyenergetic positive ion therapy system of claim 1, wherein the magnetic field is between about 0.5 and about 10 Tesla.

4. The method of treating a patient with a laser-accelerated high energy polyenergetic positive ion therapy system of claim 1, wherein the magnetic field is between about 0.8 and about 5 Tesla.

5. The method of treating a patient according to claim 1, wherein determining the dose distributions comprises determining the energy distribution, intensity and direction of a plurality of therapeutically suitable high energy polyenergetic positive ion beams.

6. The method of treating a patient according to claim 1, wherein said therapeutically suitable polyenergetic positive ion beams are prepared by:
    forming a laser-accelerated high energy polyenergetic ion beam comprising high energy polyenergetic positive ions;
    collimating said laser-accelerated high energy polyenergetic ion beam using at least one collimation device;
    spatially separating said high energy polyenergetic positive ions according to their energy levels using a first magnetic field provided by one of the superconducting electromagnets;
    modulating the spatially separated high energy polyenergetic positive ions using an aperture; and
    recombining the modulated high energy polyenergetic positive ions using a second magnetic field provided by a superconducting electromagnet different than the one used for providing the first magnetic field.

7. The method of treating a patient according to claim 6, wherein the modulated high energy polyenergetic positive ions have energy levels in the range of from about 50 MeV to about 250 MeV.

8. The method of treating a patient according to claim 6, wherein the high energy polyenergetic positive ions include light ions including protons, lithium, boron, beryllium, or carbon, or any combination thereof.

9. The method of treating a patient according to claim 6, wherein the trajectories of the high energy polyenergetic positive ions are bent away from a beam axis of said laser-accelerated high energy polyenergetic ion beam using said first magnetic field.

10. The method of treating a patient according to claim 9, wherein the trajectories of the spatially separated high energy polyenergetic positive ions are bent towards the aperture using a third magnetic field.

11. The method of treating a patient according to claim 10, wherein the spatially separated high energy polyenergetic positive ions are modulated by energy level using a plurality of controllable openings in said aperture.

12. The method of treating a patient according to claim 11, wherein the trajectories of the modulated high energy polyenergetic positive ions are further bent towards the second magnetic field using said third magnetic field.

13. The method of treating a patient according to claim 12, wherein the trajectories of the modulated high energy polyenergetic positive ions are bent towards a direction parallel to the direction of a beam axis of the laser-accelerated high energy polyenergetic ion beam using said second magnetic field.

14. The method of treating a patient according to claim 6, wherein a portion of the recombined high energy polyenergetic positive ions are fluidically communicated through a secondary collimation device.

15. The method of treating a patient according to claim 14, wherein the beam shape of the recombined high energy polyenergetic positive ions is modulated by the secondary collimation device.

16. A laser-accelerated high energy polyenergetic positive ion beam treatment center, comprising:
a location for securing a patient; and
a laser-accelerated high energy polyenergetic positive ion therapy system capable of delivering a therapeutically suitable high energy polyenergetic positive ion beam to a patient at said location, the ion therapy system comprising:
a laser-targeting system, said laser-targeting system comprising a laser and a target assembly capable of producing a high energy polyenergetic ion beam, comprising high energy polyenergetic positive ions having energy levels of at least about 50 MeV;
an ion selection system capable of producing a therapeutically suitable high energy polyenergetic positive ion beam using said high energy polyenergetic positive ions, the high energy polyenergetic positive ions being spatially separated based on energy level using superconducting electromagnets each capable of providing a magnetic field of between about 0.1 and about 30 Tesla; and
a monitoring and control system for said therapeutically suitable high energy polyenergetic positive ion beam.

17. The laser-accelerated high energy polyenergetic positive ion beam treatment center of claim 16, wherein the magnetic field is between about 0.2 and about 20 Tesla.

18. The laser-accelerated high energy polyenergetic positive ion beam treatment center of claim 16, wherein the magnetic field is between about 0.5 and about 10 Tesla.

19. The laser-accelerated high energy polyenergetic positive ion beam treatment center of claim 16, wherein the magnetic field is between about 0.8 and about 5 Tesla.

20. The laser-accelerated high energy polyenergetic positive ion beam treatment center of claim 16, wherein the ion selection system comprises:
a collimation device capable of collimating said high energy polyenergetic ion beam;
a first magnetic field source capable of spatially separating said high energy polyenergetic positive ions according to their energy levels, said first magnetic field source provided by one of the superconducting electromagnets;
an aperture capable of modulating the spatially separated high energy polyenergetic positive ions; and
a second magnetic field source capable of recombining the modulated high energy polyenergetic positive ions into said therapeutically suitable high energy polyenergetic positive ion beam, the second magnetic field provided by a superconducting electromagnet different than the one that provides the first magnetic field.

21. The laser-accelerated high energy polyenergetic positive ion beam treatment center of claim 20, wherein the modulated high energy polyenergetic positive ions are characterized as having energy levels in the range of from about 50 MeV to about 250 MeV.

22. The laser-accelerated high energy polyenergetic positive ion beam treatment center of claim 20, wherein the high energy polyenergetic positive ions include light ions including protons, lithium, boron, beryllium, or carbon, or any combination thereof.

23. The laser-accelerated high energy polyenergetic positive ion beam treatment center of claim 20, wherein said first magnetic field source is capable of bending the trajectories of the high energy polyenergetic positive ions away from a beam axis of said laser-accelerated polyenergetic ion beam entering the first magnetic field.

24. The laser-accelerated high energy polyenergetic positive ion beam treatment center of claim 23, wherein the ion selection system further comprises a third magnetic field source capable of bending the trajectories of the spatially separated high energy polyenergetic positive ions towards the aperture.

25. The laser-accelerated high energy polyenergetic positive ion beam treatment center of claim 24, wherein the aperture is placed outside of the magnetic field of said third magnetic field.

26. The laser-accelerated high energy polyenergetic positive ion beam treatment center of claim 24, wherein the magnetic field of said third magnetic field source is capable of bending the trajectories of the modulated high energy positive ions towards the second magnetic field source.

27. The laser-accelerated high energy polyenergetic positive ion beam treatment center of claim 26, wherein the second magnetic field source is capable of bending the trajectories of the modulated high energy polyenergetic positive ions towards a direction parallel to a beam axis of the laser-accelerated high energy polyenergetic ion beam.

28. The laser-accelerated high energy polyenergetic positive ion beam treatment center of claim 23, further comprising a secondary collimation device capable of fluidically communicating a portion of the recombined high energy polyenergetic positive ions therethrough.

29. The laser-accelerated high energy polyenergetic positive ion beam treatment center of claim 20, wherein said aperture comprises a plurality of openings, each of the openings capable of fluidically communicating ion beamlets therethrough.

30. The laser-accelerated high energy polyenergetic positive ion beam treatment center of claim 16, wherein the target assembly and the ion selection system are placed on a rotating gantry.

31. The laser-accelerated high energy polyenergetic positive ion beam treatment center of claim 16, wherein a laser beam of said laser is reflectively transported to the target assembly using a plurality of mirrors.

32. The laser-accelerated high energy polyenergetic positive ion beam treatment center of claim 31, wherein the ion selection system is robotically mounted to give permit scanning of the therapeutically suitable high energy polyenergetic positive ion beam.

33. The laser-accelerated high energy polyenergetic positive ion beam treatment center of claim 31, further comprising at least one beam splitter to split the laser beam to each of at least two target assemblies.

34. The laser-accelerated high energy polyenergetic positive ion beam treatment center of claim 16, wherein the laser-targeting system comprises a plurality of target assemblies, each of said target assemblies capable of producing a high energy polyenergetic positive ion beam, said high energy polyenergetic positive ion beam comprising high energy polyenergetic positive ions comprising energy levels of at least about 50 MeV;

a plurality of ion selection systems each capable of individually producing a therapeutically suitable high energy polyenergetic positive ion beam from each of said individual high energy polyenergetic positive ion beams; and an individual polyenergetic ion beam monitoring and control system for each of said therapeutically suitable high energy polyenergetic positive ion beams.

* * * * *